(12) United States Patent
Dunn

(10) Patent No.: US 8,728,733 B1
(45) Date of Patent: May 20, 2014

(54) METHYL-CPG ISLAND-ASSOCIATED GENOME SIGNATURE TAGS

(75) Inventor: John J. Dunn, Bellport, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 1567 days.

(21) Appl. No.: 11/926,203

(22) Filed: Oct. 29, 2007

Related U.S. Application Data

(60) Division of application No. 10/791,074, filed on Mar. 2, 2004, now Pat. No. 7,323,306, which is a continuation-in-part of application No. 10/113,916, filed on Apr. 1, 2002, now abandoned.

(51) Int. Cl.
*C12Q 1/68* (2006.01)

(52) U.S. Cl.
USPC ......................................... 435/6.12

(58) Field of Classification Search
None
See application file for complete search history.

(56) References Cited

U.S. PATENT DOCUMENTS

| | | | |
|---|---|---|---|
| 5,508,169 | A | 4/1996 | Deugau et al. |
| 5,858,656 | A | 1/1999 | Deugau et al. |
| 2005/0059022 | A1 | 3/2005 | Ruan et al. ......................... 435/6 |
| 2005/0255501 | A1 | 11/2005 | Ng et al. ............................. 435/6 |
| 2006/0084083 | A1 | 4/2006 | Ruan et al. ......................... 435/6 |
| 2006/0084111 | A1 | 4/2006 | Ruan et al. ......................... 435/6 |

OTHER PUBLICATIONS

Dunn et al. Genome Research, 2002. vol. 12, pp. 1756-1765.*
Shiraishi et al. PNAS, 1999. vol. 96, pp. 2913-2918.*
Impey, et al., "Defining the CREB Regulon: A Genome-Wide Analysis of Transcription Factor Regulatory Regions", Cell, vol. 119, Dec. 29, 2004, pp. 1041-1054.
Ren, et al., "Genome-Wide Location and Function of DNA Binding Proteins", Science, vol. 290, Dec. 22, 2000, pp. 2306-2309.
Takai, et al., "Comprehensive Analysis of CpG Islands in Human Chromosomes 21 and 22", PNAS, Mar. 19, 2002, vol. 99, No. 6, pp. 3740-3745.

* cited by examiner

*Primary Examiner* — Celine Qian
(74) *Attorney, Agent, or Firm* — Dorene M. Price; Christine L. Brakel

(57) ABSTRACT

Disclosed is a method for analyzing the organismic complexity of a sample through analysis of the nucleic acid in the sample. In the disclosed method, through a series of steps, including digestion with a type II restriction enzyme, ligation of capture adapters and linkers and digestion with a type IIS restriction enzyme, genome signature tags are produced. The sequences of a statistically significant number of the signature tags are determined and the sequences are used to identify and quantify the organisms in the sample. Various embodiments of the invention described herein include methods for using single point genome signature tags to analyze the related families present in a sample, methods for analyzing sequences associated with hyper- and hypo-methylated CpG islands, methods for visualizing organismic complexity change in a sampling location over time and methods for generating the genome signature tag profile of a sample of fragmented DNA.

5 Claims, 5 Drawing Sheets

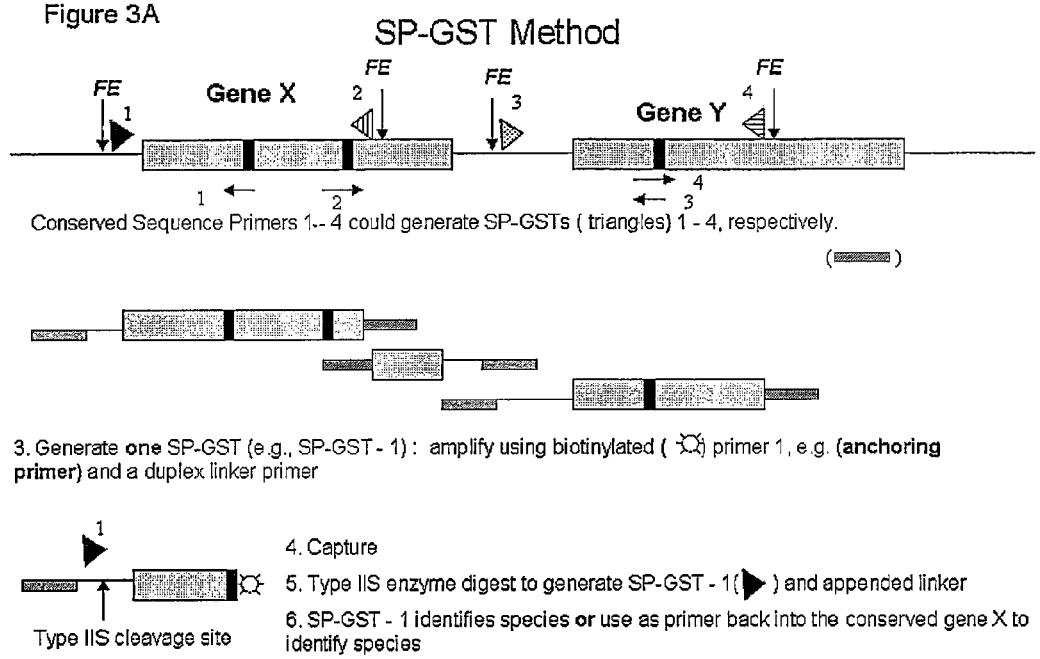
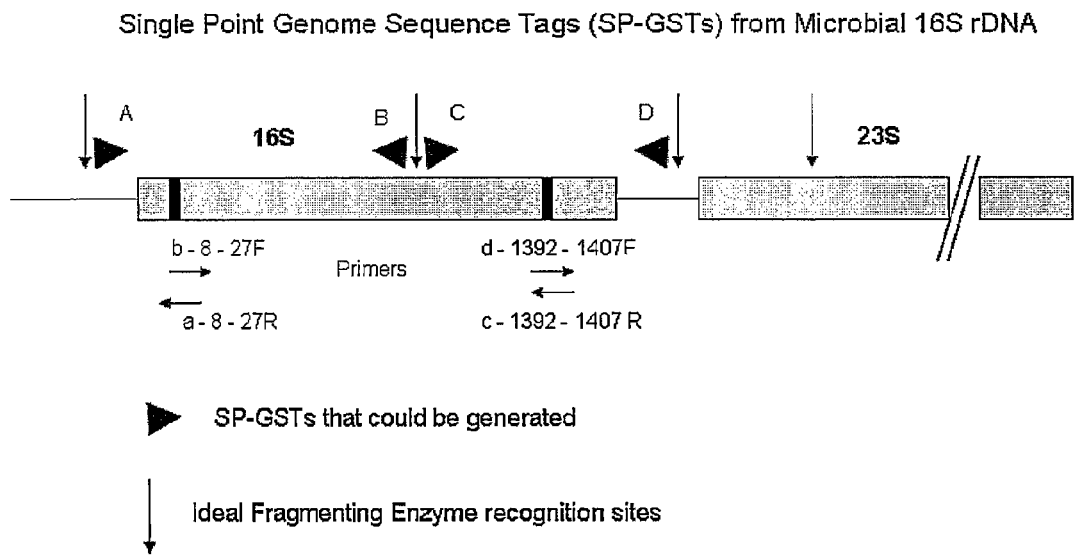

METHYL-CPG ISLAND-ASSOCIATED GENOME SIGNATURE TAGS

The present application is a divisional application of U.S. patent application Ser. No. 10/791,074, filed on Mar. 2, 2004 now U.S. Pat. No. 7,323,306, which is a continuation-in-part of U.S. patent application Ser. No. 10/113,916 filed on Apr. 1, 2002, now abandoned, the entire contents of which are incorporated by reference.

This invention was made with Government support under contract number DE-AC02-98CH10886, awarded by the U.S. Department of Energy. The Government has certain rights in the invention.

BACKGROUND OF THE INVENTION

Research toward improving the ability to detect and identify microbial genomes has risen to prominence in part because of its application to defense against bio-terrorism and biological warfare. The steadily rising numbers of sequenced microbial genomes is also giving impetus to studies of natural populations populations in soil and water, with a view to understanding community composition and dynamics. Understanding of microbial community dynamics is also important in the field of infectious disease health care, particularly in view of the rise in the prevalence of antibiotic resistant strains of microorganisms. In each of these scenarios, genomic information needs to be sufficiently detailed to distinguish among strains, and needs to provide a quantitative measure of the relative abundance of individual genomes in a sample.

In the last twenty years, a variety of DNA-based techniques have been developed to allow comparisons of whole genomes. Perhaps one of the simplest approaches involves electrophoretic separation in two dimensions to separate restriction fragments. Fischer et al. (Cell 16:191-200 (1979)) combined size separation in the first dimension with mobility in a denaturating gradient in the second dimension, to effectively separate and then probe whole-genome restriction digests.

A PCR-based method to generate fingerprint profiles of bacterial DNA by amplifying fragments generated by cutting at rare restriction sites has been developed (Masny et al. (1991) Biotechniques 31:930-936), but utility is limited to analysis of relatively small fragments.

Restriction landmark genome scanning (RLGS) is a related method in which genomic DNA is end-labeled at sites generated by cleavage with a rare-cutting restriction enzyme, followed by gel electrophoretic size separation. The fragments are cleaved in situ with a second, more frequently cutting restriction enzyme and subjected to second-dimension electrophoresis to resolve the end-labeled fragments.

Recently, Rouillard et al. (Genome Res 11:1453-1459 (2001)) developed a software tool designated virtual genome scan (VGS), that makes it possible to predict automatically the sequence of first dimension NotI plus EcoRV fragments, and second dimension HinfI or DpnII fragments in RLGS patterns of total human DNA, by matching fragment mobilities to those predicted from the draft human genome sequence. The utility of this method was demonstrated by its ability to identify a specific NotI-EcoRV fragment from human chromosome 1 that is frequently absent from restriction digests of neuroblastoma cells. Sequence prediction by VGS, as well as cloning of the fragment, showed that it contained a CpG island that is part of the human orthologue of the hamster homeobox gene Alx3 (Wimmer et al. (1992) Genes Chromosomes Cancer 33:285-94).

While VGS can provide a limited global survey for the presence or absence of a particular DNA fragment, it cannot directly identify novel sequences. VGS can be viewed as a closed architecture technique since it is inherently retrospective, relying on pre-established sequence information.

The above described methods are tools for fingerprinting genomes of individual organisms. The methods are dependent upon the integrity of the starting DNA, the completeness of the digestion by the restriction enzymes and the reproducibility of the electrophoretic separation procedures. In addition, it would be unlikely that the methods would be applicable to identifying and quantitating the multiplicity of organisms in a natural, e.g., environmental, sample.

An open architecture, comprehensive, DNA-based method for the identification and quantitation of organisms in a sample (i.e., the organismic complexity of a sample) would find many applications. One such application relates to the identification and quantitation of organisms adapted for bio-terrorist activities, while another relates to the identification and quantitation of organisms comprising a biofilm or those contained in a biological or other natural specimen and the dynamic population changes occurring in such samples over time. Population-differences and changes in spatial distributions of organisms can also be demonstrated with such a system. Such a system would be particularly advantageous for identifying and quantifying organisms that are difficult to cultivate.

SUMMARY OF THE INVENTION

The present invention relates to a method for analyzing the nucleic acid prepared from a specimen to establish the organismic organismic complexity of the sample and to quantify changes in the organismic complexity over time. In the disclosed method, nucleic acid prepared from a specimen is converted to double-stranded DNA, if necessary, and is then contacted with a type II restriction enzyme (the fragmenting enzyme), under conditions appropriate for complete digestion of the DNA by the type II restriction enzyme. This digestion generates a plurality of DNA fragment species, each DNA fragment species having identical complementary cohesive termini. A capture adapter, covalently modified with a first member of a specific binding pair, is then ligated to the cohesive termini of the fragment species. The ligation products are cleaved by digestion with an anchoring restriction enzyme, said enzyme having a high probability of cleaving a substantial number of the DNA fragment species at least one time. These digestion products are captured by contacting the cleaved products with a solid support having an attached second member of the specific binding pair. The captured products are incubated with a molar excess of a duplex linker having a type IIS restriction enzyme recognition sequence and one cohesive terminus compatible with termini generated by the anchoring enzyme, under conditions appropriate for ligating one duplex linker to the cohesive termini of the captured digestion products, thereby providing a recognition sequence for the type IIS restriction enzyme. This ligation product, still bound to the solid support, is incubated bound to the solid support, is incubated with a type IIS restriction enzyme, thereby generating and releasing the genome signature tags (GSTs) which are analyzed as described herein.

Various embodiments of the present invention, some of which include changes in the order in which various adapters and linkers are deployed relative to the general method, provide additional versatility and utility to the genome signature tags method. The various embodiments include methods for analyzing organismic complexity through the identification and analysis of single point genome signature tags (SP-GSTs), methods for analyzing sequences associated with hyper- and hypo-methylated CpG islands in genomic DNA, methods for generating terminal restriction fragment barcodes for studies of population changes in a sampling site and methods for generating the GST profile of a sample when the sample DNA is fragmented. The latter method is applicable to poorly preserved DNA-containing samples and to samples in which the DNA was fragmented for purposes of analyzing chromatin structure, including the analysis of binding sites for transcription factors.

BRIEF DESCRIPTION OF THE DRAWINGS

FIG. 3 is a schematic representation of the use of the Single Point GST (SP-GST) methods. FIG. 3A outlines the method as applied to conserved Genes X and Y and FIG. 3B represents the SP-GST method as applied to microbial rDNA genes.

DETAILED DESCRIPTION OF THE INVENTION

Overview

Figure 1:
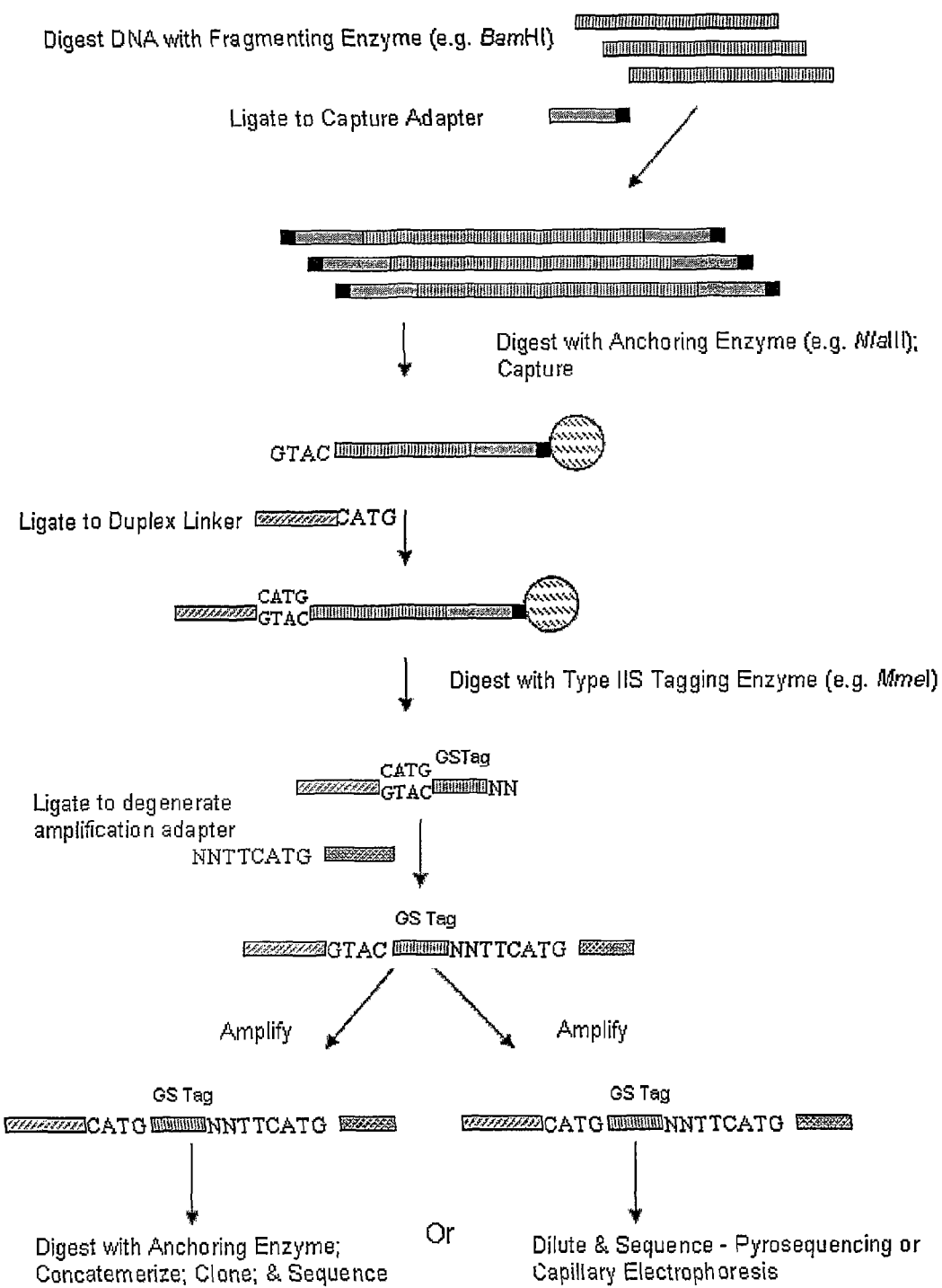
FIG. 1 is schematic representation of the generalized methods of the present invention.

Disclosed herein is a method for obtaining and analyzing signature tags from nucleic acid samples prepared from specimens of various types and to use that analysis to identify and quantify the variety of organisms contributing to the nucleic acid sample (i.e., determining the organismic complexity of a sample). One aspect of the present invention relates to a cloning-independent method for analyzing the nucleic acid sample. Another aspect of Another aspect of the invention relates to the use of the GST methods to identify sequences that are hyper- (or hypo-) methylated. Yet another aspect of the invention relates to the use of subsets of GSTs to identify and quantify members of families of organisms contributing to the organismic complexity of a sample. Another aspect of the invention relates to generating a Terminal Restriction Fragment Barcode from sequences associated with GSTs to monitor stability and rapidly identify the occurrence of changes in the organisms populating a sampling site. An additional aspect of the invention relates to methods for analyzing the GSTs of samples comprising fragmented DNAs.

The term signature tag, as used herein, is intended to encompass short duplex nucleic acid fragments corresponding to DNA segments of an organism. The methods of the present invention can be applied to the analysis of any organism or mixture of organisms having a single or double-stranded nucleic acid genome (i.e., RNA or DNA). The methods are well-suited to the identification and analysis of microbes, such as bacteria and viruses.

While the term genome signature tag (GST) is sometimes used herein to refer to tags that are derived from a duplex genomic sample, it should be noted that GST can also refer to tags derived from non-duplex genomes, such as genomes comprised of single-stranded RNA or DNA. Furthermore, the term signature tag, when tag, when used alone, is intended to encompass short duplex nucleic acid fragments generated from not only the genome of an organism, but also from their non-chromosomal nucleic acids, including episomal nucleic acid, organelle genomes and also the expressed RNA. In principle, the method can provide limited representation of all the nucleic acid molecules in a sample without prior knowledge of either the nucleic acid sequence or the specific organisms comprising the specimen. The approach can be fine-tuned by the user to provide different degrees of coverage and discriminatory power.

The method is similar to the TALEST protocol (Spinella et al. (1999) Nucleic Acids Res. 27:e22) in that it utilizes an adapter to attach known sequences to the ends of type IIS restriction enzyme-digested DNAs, thereby taking advantage of being able to use cohesive termini for high-efficiency adapter addition. In the exemplifications of the present invention a 16-fold degenerate amplification adapter is exemplified. However, to the extent that high efficiency ligation is not strictly required, blunt-ended ligation to a blunt end generated by a type IIS restriction enzyme or generated by blunt ending type IIS-cut DNA is intended to be encompassed within the scope of the present invention. The amplification adapter may be part of a collection which is fully degenerate so as to be compatible with all overhangs generated by the type IIS enzyme or partially degenerate degenerate so as to be selective with respect to compatibility with the generated overhangs. There is no strict requirement that the amplification adapter be incubated within the context of a collection in the ligation mixture. That is, individual amplification adapter species may be used in separate ligation mixtures if desirable. Alternatively, for non-complex samples, use of a single amplification adapter species may be sufficient. Because the amplification adapter, as exemplified herein, is in molar excess during ligation to the type IIS enzyme-generated ends, few tags should ligate to one another and then be sandwiched by the duplex linker instead of being flanked by the duplex linker and the amplification adapter. Tag panhandle structures are thereby avoided. In contrast, excess amplification adapters that dimerize during ligation are expected to form panhandles that should suppress their amplification. Other non-standard steps in the tag amplification strategy include two separate rounds of linear amplification to generate sufficient material, while at the same time reducing product heterozygosity (i.e., reducing heteroduplex formation).

One aspect of the present invention relates to a cloning-independent method for analyzing genomic DNA and, by extension, non-genomic DNA and expressed RNA. In this aspect the invention depends upon the generation of a collection of signature tags from the nucleic acid in a sample, which signature tags are then individually sequenced as described herein. The cloning-independent method relies upon limiting dilution of the mixture of signature tags to separate one from another and then individually sequencing the separated tags using methods that are particularly suited to sequencing uniformly sized, relatively short segments of DNA.

The Genome Signature Tags Method

The methods of the invention depend on the ability of a type II restriction enzyme, termed the fragmenting enzyme, to cleave the starting DNA into a manageable number of fragments, all having the same complementary cohesive single-stranded extensions. Preferably the type II restriction enzyme is one that generates a 3' or 5' overhang extension at the ends of the cleaved DNA fragments. Assuming a 50% G+C content, an enzyme such as NotI with an 8-base recognition sequence will cleave on average every $4^8$ (65.5 kb) bases compared to every $4^6$ (4 kb) bases for a restriction enzyme with a 6-base recognition sequence, such as BamHI. In practice, this means that fragmenting the DNA with BamHI, for example, will usually produce ten to sixteen times more GSTs from a genome, than would fragmentation with NotI. Other factors that influence the number of fragments generated by the fragmenting enzyme are: G+C content, dinucleotide frequency, and sensitivity to methylation. CpG methylation completely blocks cleavage by NotI, and such sites would be missed if only NotI was used for sites would be missed if only NotI was used for fragmentation. Fortunately, there are at least 10 other commercially available enzymes with specificities greater than 6 bases that can be used for GST fragmentation. Some of these enzymes, such as PacI (recognition sequence TTAAT↓TAA), cut only A+T rich DNAs while others cut primarily G+C rich DNAs, but are not sensitive to CpG methylation. The use of GST methods to analyze complex mixtures of organisms may necessitate the use of two or more fragmenting enzymes to ensure an adequate depth of GST coverage (i.e., that a statistically significant number of GSTs had been generated and sequenced so as to provide a reasonably accurate estimation of the organismic complexity of the sample).

Figure 2:
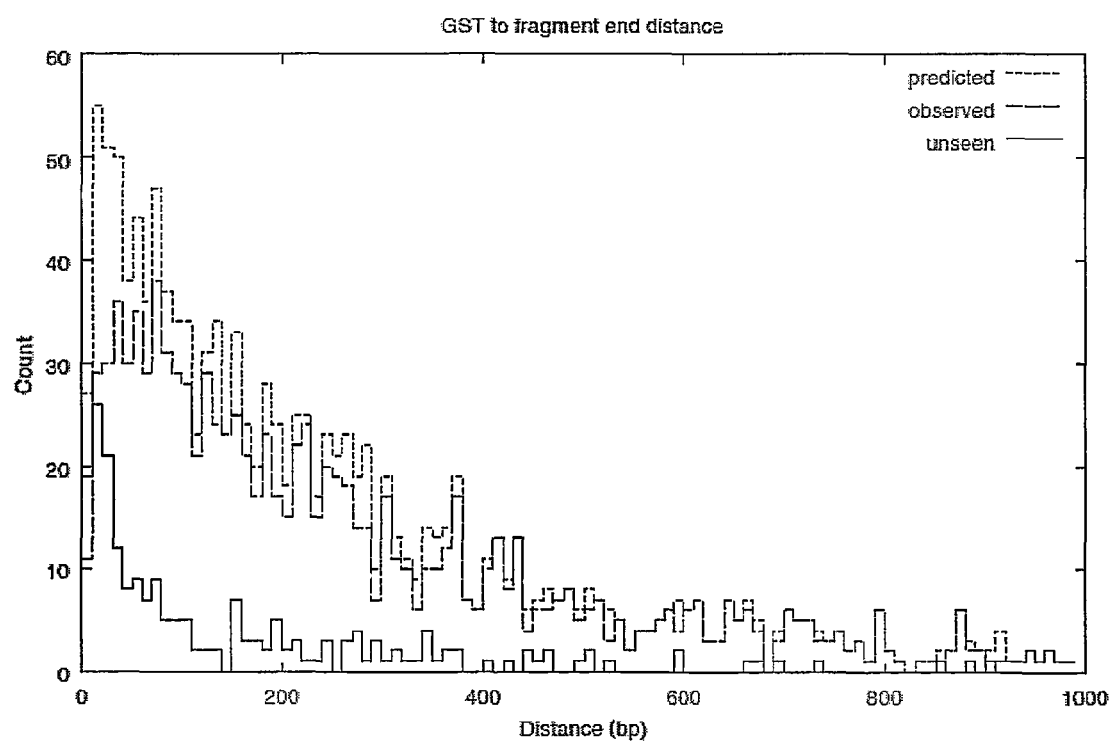
FIG. 2 represents length distribution of *Y. pestis* BamHI-NlaIII Genome Signature Tags (GSTs). The number of GSTs is plotted on the Y axis. Their lengths are plotted on the X axis. Shown are the predicted GSTs (short dashes), the observed GSTs (long dashes), and the unseen GSTs (solid line).

Fragmenting enzymes which generate cohesive termini are preferred for use in connection with the present invention. The presence of cohesive termini greatly increases ligation efficiency, for example, in connection with the addition of appropriate capture adapters, such as biotinylated capture adapters. It is believed that cohesive end-mediated ligation with a biotinylated capture adapter as opposed to enzymatically biotinylating the DNA is an important discriminatory GST tool. Cohesive end-mediated ligation with a capture adapter assures that only the ends of the DNA that were generated by the fragmenting enzyme are labeled with the capture ligand, an outcome that can be very difficult to achieve when dealing with nucleic acid isolated nucleic acid isolated from non-laboratory sources where degradation and random fragmentation is likely to have generated random ends, which would be labeled by enzymatic biotinylation. In fact, for GST analysis the starting DNA does not have to be high molecular weight since as shown in FIG. 2, even a relatively small fragment containing a site for the fragmenting enzyme should carry a nearby site for the anchoring enzymes of the present invention. One embodiment of the GST method is specifically applicable to samples comprising fragmented DNA regardless of whether fragmentation occurred as a result of poor preservation of the sample or whether fragmentation was done by the GST method practitioner for purposes such as those described herein.

Following substantially complete digestion of the genomic DNA with the type II fragmenting enzyme, the genomic DNA fragment species are ligated with a molar excess of short duplex complementary capture adapters that have only one cohesive end compatible with the termini generated by the type II restriction enzyme used to fragment the DNA. The capture adapters used in the ligation step are covalently modified with a first member of a specific binding pair, for example, biotin which binds tightly to streptavidin. Although biotin/streptavidin is a preferred binding pair, other binding pairs can be used for recovery of samples and are known in the art. Typically, the first member is linked to linked to the molecule to be recovered and the second member is attached to a solid matrix or support. For example, the capture adaptor described above can be linked to biotin. In this way, streptavidin coated beads can be used to recover the genomic, DNA fragment species that ligate to the biotinylated capture adapter. Other examples of binding pairs include, but are not limited to, antigen/antibody, sugar/lectin, apoenzyme/cofactor, hormone/receptor, enzyme/inhibitor, and complementary homopolymeric oligonucleotides. Examples of solid supports to which second members of the binding pairs can be attached include, but are not limited to, magnetic beads, glass beads, filter membranes, filter papers and polymeric beads.

After the ligation step in which individual genomic DNA fragment species are ligated to, and thereby flanked by capture adapters, each linked to a first member of a binding pair, the ligation products are digested with a restriction endonuclease that is herein referred to as the anchoring enzyme. In choosing a suitable anchoring enzyme, it is preferred that the restriction enzyme have a high probability of cleaving a substantial number of the DNA fragment species at least once. For example, a restriction enzyme having a 4-base pair (bp) recognition site, such as, NlaIII, DpnII, MboI, Tsp509I, MseI or Sau3AI, is expected to cut on average once every 256-bp and is thus a suitable anchoring enzyme. Although other enzymes can be used as anchoring anchoring enzymes, it is also preferred that digestion by the anchoring enzyme generates a cohesive terminus.

If the anchoring enzyme has at least one cleavage site present within a DNA fragment species, the DNA fragment species will be cleaved by the anchoring enzyme to generate, depending on the number of anchoring enzyme cleavage sites, at least two fragments. However, regardless of the number of anchoring enzyme recognition sites present within a DNA fragment species, cleavage by the anchoring enzyme will generate only two fragments that comprise genomic DNA sequences flanked, at one end, by a capture adapter and, at the opposite end, by the terminus that corresponds to the anchoring enzyme recognition sequence (or, a portion thereof). As described below, these fragments will be recoverable because the capture adapters are linked to the first member of the binding pair (e.g. biotin) and can bind to, and be recovered by, solid supports coated with the second member of the specific-binding pair (e.g. streptavidin-coated beads).

Following anchoring enzyme digestion, the digestion products are captured on the solid support. The support is washed and the attached digestion products are optionally re-incubated with the anchoring restriction enzyme to ensure compete digestion. The completely digested products are then ligated to a duplex linker having a cohesive terminus complementary to the cohesive terminus generated by the anchoring enzyme. The duplex linker also linker also comprises a recognition sequence for a type IIS enzyme, herein referred to as the "tagging" enzyme.

In selecting a type IIS restriction enzyme for use as a tagging enzyme, it will be recognized by one skilled in the art that a number of type IIS enzymes are available that cleave at a location remote from their respective recognition site. Longer tags are particularly useful and one very useful and preferred restriction enzyme for use as the tagging enzyme is MmeI which cleaves 20/18 bases past its non-palindromic (TCCRAC) recognition sequence (Boyd et al., (1986) Nucleic Acids Res. 14:5255-74; Tucholski et al. (1995) Gene 157:87-92). This length has suggested that MmeI could be used to obtain unique tags directly from total microbial DNA since there are $4^{21}$ or more than 4 trillion possible 21-mer tag sequences, which by far exceeds the number of 21-mers in most microbial genomes. Consequently, an MmeI tag should, in most cases, be able to uniquely identify its DNA source even in the absence of positional information. It should be noted that the fourth base (R) of the MmeI recognition sequence can be adenine or guanine.

One skilled in the art will further appreciate that additional type IIS restriction enzymes with similarly distant cutting specificities are likely to be recognized through continuing research efforts in the field of restriction enzyme biology and such enzymes would be equally useful as the tagging enzyme of the present invention.

In constructing the duplex linker, it is preferred that the sequence of the duplex linker be such that, when the linker is joined to the captured products that have been digested by the anchoring enzyme, the selected tagging enzyme recognition sequence be adjacent to or overlapping with the anchoring enzyme recognition sequence at the site of ligation. This adjacency or overlap will allow generation of tags that have maximum possible lengths when the sample is digested with the tagging enzyme. For example, in one exemplification, the anchoring enzyme and tagging enzyme are NlaIII and MmeI, respectively. In this scenario, the duplex linker is designed so that the 3' cytosine base in the MmeI recognition sequence (TCCRAC) is contributed by the 5' cytosine base of the NlaIII recognition sequence (CATG). Ligation of the duplex linker having this design also serves to orient the MmeI site such that it will cut in, the direction of the genomic DNA fragment and yield maximum tag lengths following digestion with MmeI, the released fragments containing 21 bases of sequence information from the DNA of the sample.

Where the anchoring and tagging enzyme recognition sequences cannot be made to overlap in the duplex linker cassette, it will be preferred that the sequences be positioned immediately adjacent to one another. For example, where Sau3AI (GATC) is selected as the anchoring enzyme, and the tagging enzyme is MmeI, it will not enzyme is MmeI, it will not be possible to overlap their respective recognition sequence. In this scenario, maximum tag length is achieved by producing a linker that positions the MmeI recognition sequence immediately adjacent to the Sau3AI recognition site. Finally, it will be apparent to one skilled in the art that other anchoring enzyme/type IIS tagging enzyme combinations can be employed in accordance with the present invention and that, for every specific combination, the length of the tag achievable following digestion will depend on the proximity of the tagging enzyme recognition sequence to the anchoring enzyme recognition sequence at the ligation end of the duplex linker.

Following ligation of duplex linkers to support-bound recovered products, and after washing to remove excess duplex linkers, the support is incubated with the tagging type IIS enzyme to release the duplex linkers and appended signature tags from the solid support. As described earlier, when the nucleic acid sample that is analyzed is genomic DNA the signature tag can be called. GST. These digestion products, comprising one duplex linker and an appended signature tag having a terminus generated by the tagging enzyme, are recovered and ligated with an amplification adapter or amplification adapter collection, including at least a subset of amplification adapters, having a terminus which renders it compatible with all termini generated by digestion with the by digestion with the tagging enzyme.

In another embodiment of the present invention, the duplex linker, in addition to having a type IIS restriction enzyme recognition sequence and one cohesive terminus compatible with termini generated by the anchoring enzyme, is further modified with a first member of a second specific binding pair. In this embodiment, recovery of the duplex linker with its appended signature tag is accomplished simply by capturing the released duplex linkers and their appended signature tags on a solid support that is covalently modified with a second member of said second specific binding pair.

In a preferred embodiment, the anchoring enzyme and tagging enzyme are NlaIII and MmeI, respectively. Although MmeI cuts 20 bp downstream of its recognition sequence, the released fragments contain 21 bases of sequence information from the starting DNA because, as described earlier, the last C residue in the MmeI recognition site of the duplex linker partially overlaps the NlaIII site of the bound DNA. These digestion products are recovered and ligated to an amplification adapter collection with a 16-fold degenerate 3' overhang (Spinella et al. (1999)) which renders the collection compatible with all possible two-base 3' overhangs produced by MmeI cleavage. In a preferred embodiment of the invention the amplification adapter also comprises a recognition site for the anchoring enzyme thus providing a GST flanked by anchoring enzyme restriction sites.

In another embodiment of the present invention, a subset of the amplification adapter collection, for example a subset having a four-fold or eight-fold 3' degeneracy, is ligated to a subset of the ends produced by the tagging enzyme. In this embodiment, only a subset of tags will be identified, thereby reducing the number of tags to be analyzed.

Following ligation of the amplification adapter collection, or a subset thereof wherein the subset may include a single species, the ligation products, now comprising a signature tag flanked on one end by a duplex linker and the other end by an amplification adapter, can be PCR-amplified with a pair of primers one specific for the duplex linker and the other specific for the amplification adapter. A solution containing amplified product is generated and in one embodiment of the invention, the tags are released from the adapters by digestion with the anchoring enzyme. The released tags are then ligated to form concatemers and concatemers of sufficient length are isolated by gel electrophoresis, cloned into a suitable vector and transformed into a suitable host. The transformed cells are cultured and the cloned DNAs are isolated and inserts sequenced.

In a preferred embodiment of the present invention, following amplification with the primers specific for the duplex linker and the amplification adapter, the concentration or titer of nucleic acid tags in the solution is determined in preparation for sequencing of the tags.

In circumstances in which the concentration of ligation products (i.e., concentration of the tags flanked by the duplex linker and the amplification adapter) is sufficiently high, the above amplification step can be omitted and the ligation products are directly prepared for sequence analysis as described below for the amplified ligation products.

In preparation for sequence analysis, the solution containing PCR-amplified tag fragments (or the solution containing the ligation products) can be diluted to generate a solution containing two or fewer individual members in a specific volume. In one embodiment, the dilution is based on the concentration of nucleic acid in the solution. The concentration of nucleic acid can be determined by methods known in the art, including, but not limited to, spectroscopy, dye staining, or DNA dipstick test. Because the individual DNA molecules are essentially identical in, length (tag plus flanking linker and adapter), the concentration of nucleic acid can be accurately converted to the number of individual DNA fragments per volume. Once the concentration is determined, the preparation is diluted into a PCR reaction mixture such that a specific volume of the complete reaction mixture contains either two or fewer or one or fewer individual DNA molecules.

In another embodiment, the dilution is based on the empirically determined titer of the nucleic acid in the solution. Ten-fold serial dilutions of the sample can be tested independently, preferably in triplicate, in a PCR reaction containing primers specific for the duplex linker and the amplification adapter. After thermal cycling, ethidium bromide and ultraviolet illumination can be used to detect the presence of amplicons in the individual wells. The dilution series can be sufficiently extensive to ensure that a point is reached where no amplification is observed for that dilution sample and any further dilutions of it. In this experimental procedure, an optimal dilution sample will be identified which is positive in one or two of the three triplicate wells for that sample and which provides a totally negative sample on further 10-fold dilution. In a scenario in which one microliter of each ten-fold dilution was tested in the triplicate wells, this optimal dilution sample should contain less than 10 molecules/microliter. To obtain one or fewer molecules in separate microwells, 10 microliters of the optimal dilution sample can be added to 1 ml of a PCR reaction mixture and then divided between microwells (10 microliter/well).

To obtain two or fewer molecules in separate wells, 20 microliter of the optimal dilution is added to 1 ml of a PCR reaction mixture and then divided between microwells (10 microliter/well).

Following the dilution steps described above, wherein microwells containing two or fewer, or one or fewer individual DNA molecules are generated, the individual 10 microliter samples are PCR-amplified with primers complementary to the duplex linker and amplification adapter. One of the primers may be biotinylated, or linked to another suitable first member of a binding pair, so that the PCR product prepared using one labeled primer (e.g. a biotinylated primer) can be captured on streptavidin coated beads and sequenced by solid state sequencing techniques such as pyrosequencing (Ronaghi, et al. (1998) Science 281:363-365).

Wells containing amplified DNA determined, for example, by ethidium bromide and UV light, can be sequenced directly. Direct sequencing techniques, such as pyrosequencing, can be used when the PCR products were prepared using, for example, one biotinylated primer. The biotinylated products can be captured on streptavidin-coated beads, transferred to a filter plate, denatured and the immobilized strand sequenced using the other non-biotinylated primer.

Alternatively, the same process can be used to prepare sequencing reactions for analysis by, for example, capillary gel electrophoresis, which is known in the art. To increase throughput during analysis on capillaries, samples can be electrokinetically injected in series on the same capillary by timing the interval between successive injections to be slightly longer than the time interval needed for resolution of the last nucleotide in the previous sample. In either sequencing method described above, wells containing amplicons derived from a single molecule will give clean, unambiguous sequence results while wells with more than one DNA molecule will produce mixed signals. These latter samples can be discarded unless a capillary electrophoresis system designed to analyze two sequences simultaneously is employed.

In developing the above dilution step, it was reasoned that following dilution and PCR amplification, not all wells will be positive, and negative wells may be particularly frequent in the case in which the DNA mixture was diluted to less than one molecule per reaction aliquot. In this case some wells will have received only one DNA molecule, some will have received none and a few will have received more than one. In the case in which the DNA molecule mixture was diluted to less than two molecules per reaction aliquot, many of the wells will contain one or two molecules and some wells will contain none or more than two molecules. The relative intensity of the ethidium fluorescence can be used to determine which wells originally contained more than one or more molecules.

A listing of the sequences of the individual tags is developed following sequence determination. The listed sequences are compared to sequences in databases and the organisms having the tags are noted. In the instances in which more than one organism has an identified tag, the presence of unique tags for one or more of the organisms having the tag, and the absence of unique tags for the other organisms is used to confirm the presence of specific organisms and to rule out the presence of the other organisms. Once this analysis is concluded a listing of the organisms in the sample can be prepared.

Provided sufficient genome sequence information is available for the identified organisms comprising the sample, by comparing the relative frequency of unique tags for each of the represented organisms, the relative numbers of the organisms with respect to one another in the sample can be determined. Thus, the organismic complexity of the sample is determined.

In natural sampling locations, such as field locales, medical samples or other biological specimens, performing the procedure on samples taken repetitively over a sampling period will provide a means of monitoring changes in the organismic complexity of the sampling location over time.

In another embodiment, the GST protocol provides a method for analyzing single-stranded nucleic acid, for example, poly $(A)^+$ eukaryotic mRNAs, bacterial mRNA, and single-stranded viral genomic DNA or RNA. Only minor changes in the GST protocol are needed to use the method for analysis of single-stranded nucleic acid. In these cases, double-stranded DNA is synthesized from the single-stranded nucleic acid by means of an oligonucleotide primer. The oligonucleotide primer can be linked to a first member of a binding pair and anchored to beads coated with the second member of the binding pair (Virlon et al. (1999) Proc. Natl. Acad. Sci. USA 96:15286-91). In a preferred embodiment, biotinylated oligonucleotide primers are used in conjunction with streptavidin-coated beads. If the single-stranded nucleic acid to be analyzed is poly $(A)^+$ eukaryotic mRNA, the oligonucleotide primer of choice is biotinylated oligo d(T). Following reverse transcription and second strand DNA synthesis, where single-Stranded RNA is converted to duplex DNA, the double-stranded DNA is then cleaved with the anchoring enzyme, for example NlaIII, leaving the 3' most portion of the cleaved double-stranded DNA with the cohesive overhang needed for ligation of the tagging enzyme duplex linker. All other steps then proceed as outlined for analysis of duplex genomic DNA.

It is also possible to modify the GST method to profile prokaryotic gene expression by first using biotinylated oligonucleotides to remove the bulk of the 16S and 23S rRNA in total bacterial RNA samples. A commercial kit based on this principle which is purported to be suitable for mRNA purification from a broad spectrum of Gram-positive and Gram-negative bacteria has been recently introduced by Ambion (Austin, Tex.). One approach approach would be to convert the purified bacterial mRNA into cDNA using random priming and reverse transcriptase. The cDNA could then be used to generate cGSTs to profile the expressed regions of the genome. As an illustrative example, the National Center for Biotechnology Information (NCBI) database lists 3885 genes in the chromosome of *Y. pestis* of which 664 encompass one or more complete GSTs in a BamHI-NlaIII library. The 765 GSTs from an EcoRI-NlaIII library would sample an additional 566 coding regions.

In summary, the basic GST method provides a means for genome-wide analysis of chromosomal and episomal DNAs, and by extension, for compositional analysis of natural populations. The method can be performed with equipment available in most molecular biology laboratories. With a few modifications, the method can be used as a tool for profiling gene expression. Furthermore, the present invention improves upon methods currently used for Serial Analysis of Gene Expression (SAGE) by providing methods that do not require forming concatamers of the tags, cloning and culturing of the concatamers in preparation for sequencing.

In profiling gene expression, the length of the tags is sufficient for recognizing, with BlastX, potential 7-amino acid sequences from proteins that may be of interest. These regions of DNA can then be targeted for synthesis of longer fragments for gene identification and possible expression.

Complex Mixtures

Computer simulations (FIG. 4) of virtual mixtures of organisms have shown the applicability of the method to analyzing the organismic complexity of mixed samples. In the example illustrated in FIG. 4 the GST analysis of two virtual mixtures of organisms was examined in silico for a situation in which the proportion of one of the organisms (*C. jejuni*) was increased from one virtual sampling time (or place) to the next. The GST method was simulated using SpeI (A↓CTAGT) as the fragmenting enzyme, NlaIII as the anchoring enzyme and MmeI as the tagging enzyme. The GSTs were sequenced to a depth of 1,000,000 (i.e., $10^6$ tags were sequenced). The results readily demonstrate that the number of times *C. jejuni* tags occurred (Tag frequency) changed dramatically while all others remained relatively unchanged, reflecting the significant change in the proportion of *C. jejuni* in the virtual samples.

The practicality of sequencing to a depth of 1,000,000 for any individual sample is questionable given the current state of, the art. If entirely automated, there would seem to be no difficulty in sequencing to such a depth. However, to obtain a reasonable estimate of the organismic complexity of a sample, one must develop various strategies for assuring that a statistically significant number of tags have been sequenced.

One such strategy was touched on above in which it was suggested that using more than one fragmenting enzyme for analysis of a sample would provide increased depth of coverage. One can use such an approach to estimate the accuracy of the analysis as follows. One first examines a sample using a first fragmenting enzyme, for example, a 6-cutter having no A+T or G+C specificity bias, and then develops the listing of GSTs and the listing of organisms. To verify whether or not adequate depth of coverage had been achieved one then re-analyzes the original sample using a different fragmenting enzyme, for example one having properties that differ from the first fragmenting enzyme such as an 8-cutter having an A+T-rich recognition sequence. If the two analyses result in identifying the same organisms, and reveal similar relative abundances of the various organisms, one would be assured that a statistically significant number of tag sequences had been determined and that a reasonably accurate estimate of the organismic complexity of the sample had been determined.

Another strategy can be applied when full genomic sequences are available for the organisms identified in an analysis. Analysis with a first fragmenting enzyme would yield a good indication of the numbers of different organisms comprising the sample. If the genomic sequences are available for each of the organisms, one could estimate fairly accurately the number of tags tags that would be generated when using any specific combination of fragmenting and anchoring enzymes on the DNAs of those organisms. As a rule of thumb, sequencing to a depth of approximately 5-fold (i.e., sequencing 5 times the number of expected tags) would assure that a statistically significant number of tags had been sequenced so as to provide a reasonable estimate of the organismic complexity of the sample.

In cases in which genomic sequences are not available, and in cases in which "unknowns" are found in an analysis, it is expected that the 5-fold depth analysis would be sufficient to identify a statistically significant number of tags from all organisms in the sample. The completeness of the analysis could then be estimated by analyzing the sample using a second fragmenting enzyme. If the number of organisms, and hence the number of tags, in a sample are not known, or if the genomic sequences are not available for at least one organism in a sample, one could be assured that a statistically significant number of tags have been sequenced when each tag has been sequenced about 5 times.

Subsets of GSTs for Identification and Quantitation of Phyla or Families of Genomes in a Specimen.

Provided the practitioner of the GST methods takes steps to avoid introducing biases which would compromise the quantitative aspects of the GST method, the probability of observing a given observing a given tag should closely follow the Poisson distribution. Thus, the probability of observing a tag having an abundance of 1/N while sequencing N tags is 0.63. As illustrated by the computer simulations of FIG. 4, application of the GST methods to a moderately complex system could easily require sequencing of up to $10^6$ GSTs. Clearly there is a need to minimize the amount of sequencing needed to characterize the organismic complexity of a sample.

To reduce the costs, in time and materials, it is desirable to develop a system in which the identification and relative quantification of organisms present in the sample could be determined using a minimum number of tags. When analyzing a sample the number of tags per organism is largely controlled by the fragmenting enzyme since the number of GSTs from a given organism is, to a first approximation, equal to the number of sites recognized by the fragmenting enzyme. The fragmenting enzyme can be selected freely by the user of the GST method, and one could choose to use a rare-cutting restriction enzyme in an attempt to reduce the number of generated tags. In order for an organism to generate a tag, the fragmenting enzyme must cut its DNA at least once.

However, a survey of microbial genomes in the NCBI database reveals that enzyme site frequencies vary dramatically between organisms. Rare cutters for some genomes are not rare for others for others and will completely miss still others. For example, the relatively rare cutter NotI (GC↓GGCCGC) yields only 2 GSTs from species of *Chlamydia* and *Archaeoglobus fulgidus*, but yields 1,289 GSTs from *Ralstonia solanacearum* and no GSTs at all from *Clostridium acetobutylicum, Mycoplasma genitalium* or *Buchnera aphidicola*. Thus, using a rare-cutting fragmenting enzyme would not always serve the purpose of reducing the number of GSTs generated from organisms but would certainly increase the likelihood of failing to detect some of the organisms comprising a sample.

The analysis of a complex sample would be most efficient when each organism generated a single or only a few GSTs. The identification of individual members of particular phyla or families of organisms in the sample using a minimum number of tags can be accomplished by focusing on specific loci, regions and/or genes (hereinafter referred to as "gene of focus") that are conserved across phyla or families of organisms to identify Single Point GSTs (SP-GSTs). A Single Point GST is the signature tag that is located at a terminus of a DNA fragment resulting from digestion of a gene of focus with a fragmenting enzyme. Depending upon the chosen gene of focus and the chosen fragmenting enzyme, an SP-GST could be a tag that is species-specific located upstream or downstream of the gene of focus. Provided the gene of focus was comprised of phylum- or family-wide conserved sequences as wide conserved sequences as well as highly species-specific sequences; the SP-GST could be a tag located within the gene of focus.

The SP-GST method is illustrated in FIG. 3A for two prospective genes of focus, Genes X and Y, which are comprised of sequences conserved across a phylum (dark bars) and sequences that are not conserved and are species- (strain-) specific (light bars). A type II restriction enzyme fragmenting enzyme is used to digest the DNA of the sample to produce a plurality of DNA fragments each having complementary cohesive termini. The digested DNA fragments are ligated to a duplex linker having a type IIS restriction enzyme recognition sequence and one cohesive terminus compatible with the cohesive termini generated by the fragmenting enzyme so that both termini of all fragments of the digested sample are ligated to a duplex linker. One primer, complementary to a conserved region of the gene of focus and which is covalently modified with a first member of a specific binding pair (referred to hereinafter as the anchoring primer), is used in combination with a primer specific for the duplex linker to amplify a segment of the gene of focus and, depending upon the location of the selected anchoring primer, sequences up- or downstream of the segment.

In the example shown in FIG. 3A, fragments of DNA comprising the 5' end of Gene X and the sequence immediately upstream of Gene X are amplified using anchoring primer 1 and the primer specific for the duplex linker. These primers, the conserved sequence anchoring primer and the duplex linker primer, will amplify this region for every organism of the sample in which Gene X is conserved. The amplified DNA fragments are captured on a solid support which is modified with the second member of the specific binding pair. The bound DNA is then cleaved with the type IIS enzyme to release the duplex linkers and the appended SP-GSTs. The SP-GST sequences are then determined to generate the listing of organisms in the sample having the conserved gene of focus.

If an SP-GST is not represented in any database the specific organism can be determined provided the sequence of the gene of focus for that organism is available. This is accomplished in another embodiment of the SP-GST method by using the "unknown" organism's Single Point Genome Signature Tag as a primer, in combination with a' conserved sequence primer (e.g., either primer 1 or reverse primer 2 in the example of FIG. 3A) to amplify a portion of the gene of focus. The organism can then be identified from the sequence of the gene of focus.

While the method outlined in FIG. 3A is illustrated using an SP-GST located upstream of the gene of focus, one of skill in the art will readily recognize how the SP-GST located within the gene of focus (e.g., SP-GST 2) and downstream of the gene of focus gene of focus (e.g., SP-GST 3) could be isolated to identify the various organisms comprising the sample and having conserved Gene X.

There are a number of genes that are suitable for selection as a gene of focus, including groLE (dnaK), recA, protein/virulence factors, multi-drug resistance factors, etc. bacteria having related properties, enzymes of pathways involved in those properties may be suitably conserved as well as species-specific to be used in this embodiment of the GST method. For example, in sulfate reducing bacteria, the dsr (dissimilatory sulfite reductase) gene could be used to identify GSTs 5' of the dsr gene comprising the sample, which in turn can be used to identify the sulfate reducing bacterial organisms comprising the sample.

A best known example of a candidate for use as a gene of focus are the genes encoding ribosomal RNAs. Across phyla and families, the rDNA genes are comprised of conserved and species-specific regions. The rDNA genes can be used specifically for assessing the bacterial, fungal or eukaryotic composition of organisms in a sample. In addition to the rDNAs, organelle DNA sequences are also excellent candidates for use as genes of focus for the SP-GST method.

FIG. 3B illustrates the SP-GST method for microbial rDNA genes. As in the general gene of focus method, in the example shown in FIG. 3B for bacterial rDNA, if an identified SP-GST, e.g. SP-GST A, was not in any database, SP-GST A can be used as a primer in combination with primer c (1392-1407R) to specifically amplify the 5' end of the 16S rDNA that is linked to the unidentified SP-GST of the as yet unidentified organism. The isolated amplified DNA segment will contain both highly conserved and the unique species (strain)-specific sequences and when the sequence is determined the organism will be identified, provided its rDNA sequence is found in a database.

Because the anchoring primer of this embodiment of the present invention is configured as a consensus sequence so that it can be used to prime DNA amplification from a plurality of templates having the conserved region of a gene of focus, the initial amplification steps of the SP-GST method may introduce a sampling bias. Such a bias would favor the amplification of DNA from those organisms having a conserved region that is most closely identical to the consensus primer and would disfavor amplification of DNA from organisms with less similar conserved regions. In the absence of such bias related to mismatches between the conserved sequence and the consensus anchoring primer, the results of the SP-GST method may yield information about the relative abundance of the various related organisms comprising the sample.

The SP-GST method can also provide information about the copy number of the gene of focus in the organisms. To determine the copy number of the gene of focus in the various organisms comprising the sample, the fragmenting enzyme is chosen so that a subset of the generated fragments comprise one portion that was either upstream or downstream of the gene of focus linked to a second portion having one or more conserved sequences of the gene of focus. The number of different, individual GSTs that are linked to an individual organism's gene of focus reveals the copy number of the gene of focus in that organism.

In the GST Methods section entitled rDNA SP-GST Methods for Microbial Analysis of Soil Samples, a preferred embodiment of the SP-GST method is described in detail in which a partially duplex linker, having dephosphorylated 5' termini is employed. While this is a preferred embodiment, which makes practicing the method easier, it will be obvious to one of skill in the art that a substantially duplex linker could have been used. In addition, it would be obvious that the 5' termini need not have been dephosphorylated. However, if such a duplex linker was employed, one may choose to first capture the linearly amplified anchoring primer products on a solid support prior to PCR amplification in addition to capturing the PCR-amplified products after PCR amplification.

Application of the GST Method to the Identification of CpG Islands

In addition to its use in analyzing the organismic complexity of a sample, in specific embodiments the present invention is further useful in assessing alterations in the methylation patterns of CpG islands, a phenomenon that is associated with aging, cancer and other developmental events related to the regulation of gene expression. Hypermethylation of CpG islands in the controlling elements of a gene is associated with decreased expression of the gene. The recognition of which genes are under expressed through CpG methylation and how that occurred would serve to hasten the understanding of the early molecular events in tumorigenesis. The correlation between hypermethylation of particular genes in specific tumor types may serve as a diagnostic or prognostic indicator.

There are several ways in which the methods of the present invention can be applied to a comprehensive determination of CpG island methylation in a sample. One such method makes use of MseI (T↓TAA) as the fragmenting enzyme to preserve CpG islands. To isolate hypermethylated CpG islands, the digested sample is then contacted with an affinity resin comprising a bound protein that specifically binds to Methyl-CpG sequences. A duplex linker, having a cohesive terminus compatible with the overhangs produced produced by the fragmenting enzyme, MmeI, and a site for a type IIS restriction endonuclease such as MmeI, is ligated to the methylated CpG island fragments that were bound to the resin either before or after their elution from the resin. If the ligation to the duplex, linker was carried out in solution, the ligation products can be re-bound to the affinity resin and then digested with the type IIS restriction enzyme, the tagging enzyme of the present invention, and the duplex linkers and appended GSTs associated with methyl-CpG islands are released. After ligation of an amplification adapter and amplification of the released GSTs using a primer pair comprising a primer specific for the duplex linker and a primer specific for the amplification adapter, the GSTs can be sequenced and their sequences then associated with genomic loci and with particular genes. A correlation between the methylation state of the controlling elements of the gene and the physiology of the cells of the sample can be made.

An alternative method makes use of two fragmenting enzymes, one sensitive to CpG methylation and the other insensitive to methylation to identify GSTs associated with methylated CpG islands. Fragmenting enzymes that are sensitive to CpG methylation and which recognize a sequence containing a CpG sequence will leave segments of genomic DNA containing methylated CpG sequences unfragmented. The restriction enzymes NgoMIV NgoMIV (G↓CCGGC), EagI (C↓GGCCG), NaeI (GCC↓GGC), SmaI (CCC↓GGG) and NotI (GC↓GGCCGC) would be good candidates as the methyl CpG-sensitive fragmenting enzyme. A methyl CpG-insensitive isoschizomer would then used as the second fragmenting enzyme in this embodiment to generate fragment species associated with methyl CpG islands.

In a preferred embodiment, SmaI (CCC↓GGG) and XmaI (C↓CCGGG) are used sequentially as the fragmenting enzymes to readily identify GSTs associated with CpG islands that are methylated. In this method, the sample DNA is first digested with SmaI which produces blunt ends and leaves methylated CpG islands unfragmented. The SmaI digested DNA is then digested with XmaI which is unaffected by methylation of CpG and which produces four base cohesive overhangs at the termini. The digested DNA fragments are then ligated to a capture adapter of the present invention having one cohesive terminus that is complementary to the cohesive termini produced by XmaI and which is further modified with a first member of a specific binding pair. The ligation products are then digested with the anchoring enzyme of the present invention. MseI is a preferred anchoring enzyme when examining human DNA for methylated CpG islands. After digestion with the anchoring enzyme, the fragments are captured on a solid support that is modified with the second member of the specific member of the specific binding pair. The captured fragments are optionally re-digested with the anchoring enzyme to ensure complete digestion. The bound fragments are then ligated to a duplex linker of the present invention, said duplex linker having a terminus that is complementary to the termini generated by the anchoring enzyme and which linker introduces a type IIS restriction enzyme site into the ligation product. The bound ligation product is then digested with the type IIS restriction enzyme and the duplex linkers and appended GSTs are released from the solid support. In a preferred embodiment, the type IIS enzyme is MmeI. The GST sequences are then determined as described above for the standard GST method and the sequences then correlated to specific genes. Changes in the profile of the methylation, state of the CpG islands can then be related to development, and/or disease diagnosis and progression. The tumor-specific GST loci can also be cloned and nearby candidate genes can be investigated as potential genetic or epigenetic targets associated with tumorigenesis.

Terminal Restriction Fragment Barcodes (TRFBs) of the GST Method for Simplifying Studies of Population Changes in a Sampling Site.

In utilizing the GST method to monitor population changes in a specific sampling site, depending upon the nature of the sample, the rate of change may be rapid or relatively slow. A simple simple method to identify whether changes had occurred from one sampling time to the next would be one which eliminated the necessity of sequencing the GSTs at each sampling time. The Terminal Restriction Fragment Barcode (TRFB) method was developed to address this issue.

To carry out the TRFB method, the samples are processed as for the standard GST method through ligation of the duplex linker to the captured DNA fragments on the solid support via the capture adapter of the present invention. The duplex linker of the TRFB method may be the same as the duplex linker of the standard GST method or it may also be modified by a signaling moiety, such as a fluorescein, rhodamine or other fluorescent signaling moiety or another moiety that can be identified by specific binding of a signaling moiety. To prepare the TRFB, the ligated bound fragments are digested separately with one or more restriction enzymes that are neither identical to nor isoschizomers of the fragmenting enzyme, the anchoring enzyme or the type IIS tagging enzyme used for the standard GST procedure for the sample. The released fragments are then separated by gel electrophorsis and the electrophoretic pattern of the released fragments is recorded as the TRFB for the sample.

If the sample is the first sample taken for a particular sampling site that is to be monitored, the solid support-bound material is also subjected to the full GST procedure. After the initial sampling of a sampling site and the establishment of the organismic complexity of the sample and the recordation of the starting TRFB for the sampling site, each subsequent sample is first subjected to the TRFB method. If no changes in the TRFB are identified, the GSTs need not be isolated and sequenced. However, if changes in the TRFB are identified, the GSTs are isolated and are sequenced by the methods of the present invention and the results are then correlated to the organismic complexity changes at the sampling site.

GSTs from Samples Containing Fragmented DNA

In applying the GST methods to various samples there is a need to develop methods for obtaining GSTs from samples containing severely fragmented DNA. Such damage to DNA of samples can arise as a result a number causes, including poor sample preservation and purposeful fragmentation of sample DNA as described herein below. In the former instance, specimens such as forensic specimens and/or environmental samples that were subjected to conditions unfavorable for preserving the integrity of the nucleic acid could be analyzed. Indeed, even archeological specimens, which would be unlikely to contain intact nucleic acids, could be analyzed. In the latter instance in which genomic DNA is purposefully fragmented after chromatin crosslinking and then subjected to immunoprecipitation using one or more antibodies against DNA binding proteins (see Ren, et al. (2000) Science (2000) Science 290:2306-2309) (e.g. transcription factors), the Fragmented DNA GST methods (FD-GST methods) can be used to provide genome-wide profiling of functional binding sites in DNAs.

Transcriptional activators bind to short DNA segments, the cis-regulatory or response elements, in a sequence-specific manner and activate or sometimes repress transcription of the target genes. Response elements can be located in promoter regions, but in some cases are found at sites within a gene or at sites distant from the gene that is regulated. The ability to profile the interactions of the DNA-binding regulatory transcription factors with changing conditions or states of health, etc., provides a major step in understanding the regulation of cells and tissues, their responses to stress and how dysfunction of regulatory networks is related to specific diseases.

In using the FD-GST methods to identify organisms comprising a poorly preserved specimen, the fragments of DNA isolated from the specimen are first treated to ensure that all fragment ends are flush, i.e., blunt ended. This can be accomplished using the DNATerminator End Repair Kit produced by Lucigen Corporation (Middleton, Wis.). Once blunt ended, two strategies are used to prepare signature tags, the first yielding tags from the blunt ends (the Fragment End DNA GST Method—$F_eD$-GSTs) and the second GSTs) and the second yielding internal tags (the Fragment Internal DNA GST Method—$F_iD$-GSTs).

Fragment End Tags:

For the fragment end tags, once blunt ended, the fragments are blunt end ligated to a duplex linker. The duplex linker is characterized by having only one blunt terminus and several restriction endonuclease sites, including one or more recognition sequences for type IIS restriction enzymes, one such type IIS site being located at the blunt terminus of the duplex linker and, optionally, one or more recognition sequences for type II restriction enzymes.

In the GST Methods section entitled Methods for Fragmented DNA, a preferred embodiment of the $F_eD$-GST method is described in detail in which a partially duplex linker, having dephosphorylated 5' termini is employed. While this is a preferred embodiment, which makes practice of the method easier, it will be obvious to one of skill in the art that a substantially duplex linker could be used, provided it had only one blunt end. In addition, it would be obvious that the 5' termini need not be dephosphorylated.

After ligation, the duplex DNA fragments, each comprising the fragments of DNA from the specimen flanked by duplex linkers, are then amplified using a capture primer that is specific for a portion of the duplex linker and which primer is modified with a first member of a specific binding pair. The amplified fragments are then digested with a first type IIS endonuclease tagging enzyme to produce duplex linkers each having an appended signature tag.

The released linkers and appended tags are then ligated to a degenerate amplification adapter. The ligation products are then amplified using a pair of primers, comprising a first primer which is specific for the duplex linker and which is modified with a first member of a specific binding pair and a second primer which is specific for the amplification adapter.

Once amplified, the sequences of the tags are determined by the methods of the general GST procedure. The listing of sequences can then be used to identify the organisms originally comprising the specimen.

Fragment Internal Tags:

For fragment internal tags, once blunt ended, the fragmented DNA is blunt end ligated to a capture adapter having a covalently attached first member of a specific binding pair at one terminus and a blunt duplex end at the other terminus. Following ligation, the fragmented DNA is flanked by the capture adapter and, optionally, can be amplified by use of primers specific for the capture adapter, which primers are also labeled with the first member of the binding pair.

In the GST Methods section entitled Methods for Fragmented DNA, a preferred embodiment of the $F_iD$-GST method is described in detail in which a partially duplex capture adapter, having dephosphorylated 5' termini is employed. While this is a preferred embodiment, which makes practice of the method easier, it will be obvious to one of skill in the art that a substantially duplex capture adapter could be used, provided it had only one blunt end. In addition, it would be obvious that the 5' termini need not be dephosphorylated.

The ligation/amplification product is then digested with the anchoring enzyme of the present invention. The digested DNA is then contacted with a solid support having an attached second member of the specific binding pair and, optionally, the captured DNA is re-digested with the anchoring enzyme to ensure complete digestion.

The captured DNA is then ligated to a duplex linker of the present invention, said duplex linker having a restriction site for a type IIS restriction enzyme located near, adjacent to or overlapping with the cohesive terminus compatible with the ends produced by the anchoring enzyme. The bound ligation products are digested with the type IIS enzyme specific for the duplex linker (the tagging enzyme) and the duplex linker and appended internal tags are released from the solid support.

The released linkers and appended tags are then ligated to a degenerate amplification adapter of the present invention and the the ligation products are amplified as in the general GST method. Once amplified, the sequences of the tags are determined by the methods of the general GST procedures.

In the GST Methods section entitled Methods for Fragmented DNA, preferred embodiments are described in detail in which degenerate, partially duplex Y-shaped amplification adapters are used in the fragmented DNA procedures. The Y-shaped adapters have one terminus that is compatible with all possible ends produced by the tagging enzyme, the other terminus comprising non-complementary sequences such that the ligation products are the signature tags flanked by the duplex linker and the Y-shaped partially duplex amplification adapter. While this preferred embodiment makes the practice of the FD-GST methods easier, it will be obvious to one of skill in the art that a substantially duplex amplification adapter, similar to that employed in the general GST procedure, could be employed in the FD-GST procedure.

In applying the $F_eD$-GST or the $F_iD$-GST method to identify tags from regions of DNA that are associated with DNA binding proteins such as transcription factors, the methods are carried out on DNA that was fragmented by sonication or other shearing method after in situ crosslinking to covalently fix DNA binding proteins to the DNA sequences to which they were bound. The fragmented DNA with crosslinked proteins are then fractionated by immuno-precipitation using an antibody that specifically binds to a specific DNA-binding regulatory protein of interest, e.g. p53. Once fractionated, the crosslinking of the immuno-precipitated fragments and their bound protein(s) is reversed and the released DNA fragments are analyzed by one or both of the FD-GST methods outlined above. The tags are sequenced, correlated to the genomic location of the tag and hence to the gene(s) that is regulated by the specific DNA-binding regulatory protein of interest.

EXEMPLIFICATIONS

Analysis of a *Y. pestis* BamHI Genomic Signature Tag (GST) Library

To optimize the laboratory procedures for practicing the basic GST method on biological specimens, *Y. pestis* was chosen as a model organism. Shown in Table 1 are the predicted numbers of tags which would be generated at each step of the procedure from *Y. pestis* DNA, using either NotI or BamHI as the fragmenting enzyme, and NlaIII and MmeI as the anchoring and tagging enzymes, respectively. Using the 4.7 Mb, *Y. pestis* CO92 complete genome (minus the pCD1 plasmid) as input (Parkhill et al. (1991) Nature 413:523-7), it was determined in silico that there should be 64 cleavage sites for NotI, 699 sites for BamHI, and 16,572 sites for NlaIII. Only one NotI fragment is predicted to lack an internal NlaIII site, but 36 of the smaller fragments generated by BamHI by BamHI should not be cleaved by NlaIII. The mean lengths of the resulting NotI-NlaIII and BamHI-NlaIII fragments are 273 and 267 bp, respectively. The similarity in these mean fragment lengths reflects both the high density and nearly random distribution of NlaIII sites in the *Y. pestis* genome. Only 11 of the NotI-NlaIII and 90 of the BamHI-NlaIII fragments are predicted to be less than 21 bp long, all other fragments should generate full-length 21 bp tags. If only 21 bp tags are considered, then the NotI-NlaIII library should sample about 2.4 kb of the *Y. pestis* sequence, while the BamHI-NlaIII library would sample about 10 times more DNA, about 26 kb.

One problem, that is intrinsic to the method, occurs when an MmeI recognition sequence (TCCRAC) of the organism being analyzed is within 21 bp of the NlaIII site. This sequence could direct cleavage back towards the NlaIII end allowing MmeI to potentially cut within the attached MmeI linker which would interfere with subsequent PCR amplification. A TCCRAC sequence within the next 21 bp could potentially give rise to tags less than 21 bp long depending upon which site is first recognized by MmeI. Analysis of the *Y. pestis* sequence indicates that MmeI digestion would at most eliminate only 17 tags from a BamHI library, but none from the NotI-derived library. While all of the 21 bp NotI derived tags are unique, 47 of the BamHI derived 21 bp tags come from 14 repeated sequences, and therefore occur two or more times within two or more times within the database.

To validate the generality of this method, a *Y. pestis* GST library was prepared using BamHI as the fragmenting enzyme since it will generate sufficient tags for meaningful data analysis. Sequence analysis of the initial library showed that MmeI can liberate both 21 and 22 bp long tags from the same location in the DNA. Analysis of this library, which was prepared using a single NlaIII digestion step, also revealed the presence of a large fraction of tags originated from NlaIII sites that were not proximal to a BamHI site. The presence of these tags in the library obviously was the result of incomplete NlaIII digestion. Therefore, a second NlaIII digestion step is now routinely included after the biotinylated fragments are captured on the magnetic beads in order to obtain more complete digests. The data reported here are from a single library prepared following the steps outlined in FIG. 1 using the concatemer formation, cloning and sequencing methods.

The capture adapter used to biotinylate the BamHI digest adds 12 bp to the ends of each fragment. In principle, the addition of this adapter should allow MmeI to liberate 21 bp long tags even from the 90 BamHI-NlaIII fragments that are less than 21 bp long. In these cases, MmeI would have to cleave within the attached adapter. Tags from these sites are easy to identify as they should contain a BamHI recognition sequence near their 3' ends. To simplify discussion, fragments are numbered according to their order along the DNA and use. R (reverse) and F (forward) to indicate the relative location of the GST within the fragment. Thus, R314 indicates the reverse GST from BamHI fragment number 314, which would be followed by F314 (the next forward GST), R315, F315, etc.

A total of 5,432 GSTs were extracted from the sequenced arrays. The number of 21 and 22 bp long tags was approximately equal, 2,701 and 2,731 respectively. The vast majority, 5,268 (97%), exactly matched at 1,133 sites in the *Y. pestis* genome. This includes a total of 336 tags which were uniquely matched at 88 correct tagging sites, even though their initial polarities were ambiguous. Most of these unique matches could be assigned to the first NlaIII site next to a BamHI fragmentation site, which indicates that the two step NlaIII digestion was virtually complete. Only 59 (1%) of the extracted tags exactly matched, interior NlaIII sites. These tags could result from over-digestion with BamHI or partial NlaIII digestion. However, it is thought that several may have arisen because subtle changes in the genome introduced new BamHI sites. This seems to be the case for fragments 90 and 459, which each gave rise to two internal tags. Two other internal tags occurred twice, which, because of the large number of total NlaIII sites in the *Y. pestis* DNA, is a highly improbable random event. A small number of tags (6) that passed all of the editing criteria, have no obvious close match to the *Y. pestis* genome or any other sequence in GenBank. These might originate from sequences that are unique to the EV766 genome or represent spurious tags generated during library construction, amplification, and cloning. Of the total predicted potential tagging sites, 209 were still unseen. It is believed that many, but not all, of these unseen sites would be matched if the sample size were increased (see discussion of unseen tags, below).

To a first approximation, isolation and sequencing of GSTs should be random processes, and on average, the relative frequency of occurrence of a particular GST in a library should reflect its frequency in the DNA sample. Therefore, tags from highly repetitive regions of the chromosome, or from higher copy number plasmids, should be more numerous than tags from unique regions. This prediction seems to hold true for the GST library. As shown in Table 2, the most abundant tag encountered is the one predicted to occur most frequently (8 times) in the *Y. pestis* chromosome. It was followed in order by the tag predicted to be the next most frequent, the one occurring 7 times. Only one tag should be present 5 times, one 4 times, three tags should each be found three times, and seven tags should each occur twice. Two other redundant tags listed in Table 2 should not be recovered at all since each contains a BamHI fragmentation site very close to its its 5' end. The actual observed frequency of the multiple tags is highly correlated (r=0.88) with the predicted frequency. However, one tag that is predicted to be present 4 times in the genome seems to be under represented in the database. This tag is associated with an IS100 element that is known to be a source for genetic variability in different *Y. pestis* isolates (Motin et al. (1992) J Bacteriol 184:1019-27), which may in part explain these results. The two plasmids, pMT1 and pPCP1, thought to be present in the EV766 Strain, each contain a single BamHI site and each should have contributed two unique tags to the library. All four tags were catalogued at about the same frequency as single-copy chromosomal tags. This would suggest that neither of these plasmids had a significantly elevated copy number in the strain used here, a prediction that was confirmed by inspection of agarose gel profiles of the total DNA used for this study.

Such deviations in tag frequency or occurrence can also occur when sequence changes introduce or remove a fragmenting site or tagging site. Loss or gain of a single fragmenting site will at most affect the two GSTs flanking the site. Deletions or insertions on the other hand can simultaneously remove or add several tags. Analysis of the data for the absence of adjacent tags revealed several places where deletions must have occurred in the EV766 genome (Table 3). The most striking example is the failure to recover any of the expected 25 consecutive tags from a segment beginning with F314 and ending with F327 (bp 2,172,627 through 2,254,447 if the 3' position of BamHI site 327 is included). This region contains a 37 kb high-pathogenicity island encoding virulence genes involved in iron acquisition from the host via a siderophore called yersiniabactin (the ybt biosynthetic gene cluster) (Buchrieser et al. (1999) Infect Immun 67:4851-61). It is part of a larger, 100 kb region termed the pgm (pigmentation) locus. This locus can delete spontaneously, probably by homologous recombination between its two flanking IS100 elements (Fetherston et al. (1992) Mol Microbiol 6:2693-704). Such a deletion would eliminate tags F314-F327; therefore, it is proposed that strain EV766 lacks the entire pgm locus. Similar analysis also identifies a potential deletion of the region bounded by R194—R197, which normally harbors an IS1541 insertion element. Deletions or other changes may have eliminated tags F237-F238, another region associated with an IS100 element. Several other regions not associated with known IS elements that also seem to have been deleted or undergone DNA rearrangements that eliminate consecutive, tags are listed in Table 3. If these 44 tags are excluded, the number of unseen tags drops to 144.

A small fraction of catalogued tags, totaling 164 (3%), appears to contain point mutations. Inspection of the relevant single-pass sequencing chromatograms indicates that the original base calls were accurate. In nearly every case, the corresponding correct GST could be found in the dataset. Presumably these differences represent errors introduced during library preparation, rather than true polymorphisms in the DNA sample. The distribution of mismatches within the tags was not totally random. Discrepancies were somewhat more frequent within the last two bases at the 3' end of the tag. This most likely reflects mis-ligation between the MmeI overhangs and the 16-fold degenerate amplification adapter during this step in the GST protocol. Increased fidelity should be possible by using a lower concentration of the degenerate amplification adapter, shorter incubation times, or higher temperature during the ligation step. One empirical way to eliminate most of these errors is to omit tags encountered only once from further analysis, as is typically done to help eliminate sequencing and other errors from SAGE libraries. This type of filtering would eliminate all but 23 of the imperfectly matched tags from further consideration.

The sequence complexity and length of a GST, 21-22 bp, should in most cases be sufficient to enable its use directly as a primer to amplify the stretch of DNA between the tagging site and the proximal site for the fragmenting enzyme. To test this concept, a group of five tags predicted to begin approximately 100 to 1000 bp away from their proximal BamHI sites were selected and were synthesized for use as primers. Template *Y. pestis* DNA was was digested with BamHI and ligated with a cassette that introduced an identical priming site at the both ends of each fragment. The DNA was then digested with NlaIII to physically separate the cassette ligated BamHI ends. Aliquots were then subjected to ten rounds of linear PCR amplification using just the GST-specific primer to increase the amount of complementary single-stranded targets in the sample. This step was then followed by twenty-five. PCR cycles with the GST primer and the BamHI cassette primer. Each reaction generated a distinct band of the expected length. Direct sequencing of these five bands unequivocally confirmed their correct location in the *Y. pestis* genome demonstrating that the GSTs are of sufficient length and complexity for use as primers.

While the data obtained show that desired objectives were obtained, further analysis (FIG. 2) suggests that under sampling of tags that lie a short distance from the fragmenting site may be occurring. This deficiency can be easily addressed by increasing the length of the biotinylated capture adapter used to attach the DNA to the streptavidin beads. In this context it is worth noting that Wang et al. (Proc. Natl. Acad. Sci. USA 95:11909-94 (1998)) observed a SphI site (GCATG↓C) tethered to a streptavidin bead by a short linker could be cut with SphI, but not by NlaIII, even though the linker contained a CATG sequence.

A critical step contributing to the robustness of the GST protocol is the amount of material produced during the first round of PCR amplification. Typically, when this reaction is analyzed by electrophoresis on a 10% polyacrylamide gel, a band with the expected mobility of the GSTs plus attached linker and amplification adapter arms, 94 bp, is observed, plus varying amounts of diffuse material with slower mobilities. The amount this diffuse material in the reaction seemed to be proportional to the number of PCR amplification cycles. Therefore, it was reasoned that it most probably represents amplicon heteroduplexes, formed by preferential perfect annealing of the low complexity linker and adapter arms, but imperfect annealing of the internal tags at high product concentrations. As expected, the bulk of this material was sensitive to digestion with S1 nuclease (data not shown). To optimize amplicon recovery, a linear amplification step was introduced to reduce heteroduplex formation (LARHD). LARHD uses one extra round of amplification to convert the bulk of the reaction products to double-stranded DNA. Several additional tests showed that the potential to form heteroduplexes could be avoided during additional rounds of PCR amplification of the LARHD products by doing repeated rounds of linear amplification with one specific primer followed by one final amplification step after addition of the second primer. Unwanted PCR primers that would be carried over from the LARHD step are eliminated by incubation with Exo I, which preferentially hydrolyzes any remaining single- which preferentially hydrolyzes any remaining single-stranded primers (Hanke et al. (1994) Biotechniques 17:858-60). Digestion with Exo I is also used to hydrolyze any free primers after the final amplification steps, prior to digestion with NlaIII to release the internal identifier tags from their flanking GST linker and amplification adapter cassettes.

Since the primers used in amplification are biotinylated at their 5' end, streptavidin beads can be used to capture the liberated cassettes, thereby avoiding losses that would accompany gel purification of the 19-bp long tags (Powell et al. (1998) Nucleic Acids Res 26:3445-6).

Mathematical Probability of Observing Tags

The only mathematical assumption behind the GST method is that the probability of observing specific GSTs should closely follow the Poisson distribution. Therefore, the probability of observing a given tag with 1/N abundance while sequencing N tags is 0.63. Tags with abundance larger than 1/N should be sampled more frequently, provided that the PCR amplification is not biased, which would compromise the quantitative aspects of the method. In developing the GST method, several steps were critically evaluated to help ensure that the frequency of tags in the library reflects the frequency of tags in the genomic DNA from which the tags were derived. The frequency distribution of the tags in the Y. pestis database appears to be quite flat, and as as might be expected, many of the most abundant GSTs were derived from repetitive sequences. This means that the technique should, in addition to being able to identify DNA sources, be able to provide a fairly accurate means for quantitative analysis of mixed DNA populations and, therefore, mixed organisms comprising a sample. This concept is currently being tested by preparing a NotI-NlaIII GST library using DNA isolated from a non-stoichiometric mixture of five different bacteria strains. The data show that 21 bp GSTs can be used efficiently as primers to PCR amplify the DNA between specific tagging and fragmenting sites. In fact, in one embodiment of the present invention using the GSTs as primers greatly facilitated the analysis of complex mixtures of organisms. The GSTs provide an upstream entry into genes (rRNA genes and specific protein coding genes) that are used to quickly identify the organisms in a complex mixture. Because this method allows one to focus on one or more specific portions of genomes, it effectively reduces the numbers of tag sequences that need to be determined.

In addition, the sequence of the products synthesized using the GSTs as primers can then be used to provide more information for deeper phylogenetic analysis of genomic samples, or as hybridization probes to facilitate isolation of complementary clones from whole genome libraries. Since. GST analysis is a direct PCR-based DNA sequencing approach for profiling DNA, it profiling DNA, it could be applied to analyze DNA composition in complex mixtures, and it could circumvent the need to isolate and grow organisms for measurement of microbial diversity and distribution in natural communities. This information could be used in conjunction with traditional culture techniques, to help complete the catalogue of species present in a sample.

Complex Samples

The results of the above study show that the GST technique provides a route to obtaining numerous 21-22 bp signature tags that can be used to identify the nucleic acid source, and as shown, the presence or absence of particular tags can provide some indication of the genetic variability between two closely related strains. The lengths of the tags allow direct determination of the source nucleic acid if the sequence is available in a database.

In silico comparison of all the BamHI-NlaIII GSTs that would be generated from a mixture of the 60 complete microbial genomes in the NCBI database demonstrated that these different bacterial strains share few GSTs in common. Table 4 contains a list of the top 30 shared tags. The worst case scenario is the occurrence of a single tag that was found three times in E. coli and once in Y. pestis. No GST was shared by three strains, although this might change as more closely related organisms are sequenced. Even between closely related strains, the frequency of unique, unshared of unique, unshared identifiers is more than adequate to allow strain differentiation. A comparison between the 4.6 Mb E. coli K12 and 5.5 Mb O157H7 genomes predicts that they would generate 863 and 1018 unique BamHI-NlaIII GSTs, respectively. While they share 554 common tags which would classify the DNA as being E. coli, the K12 genome has 309 unique GSTs, and the O157H7 genome has 464 that may be used to accurately differentiate between them.

Figure 4:
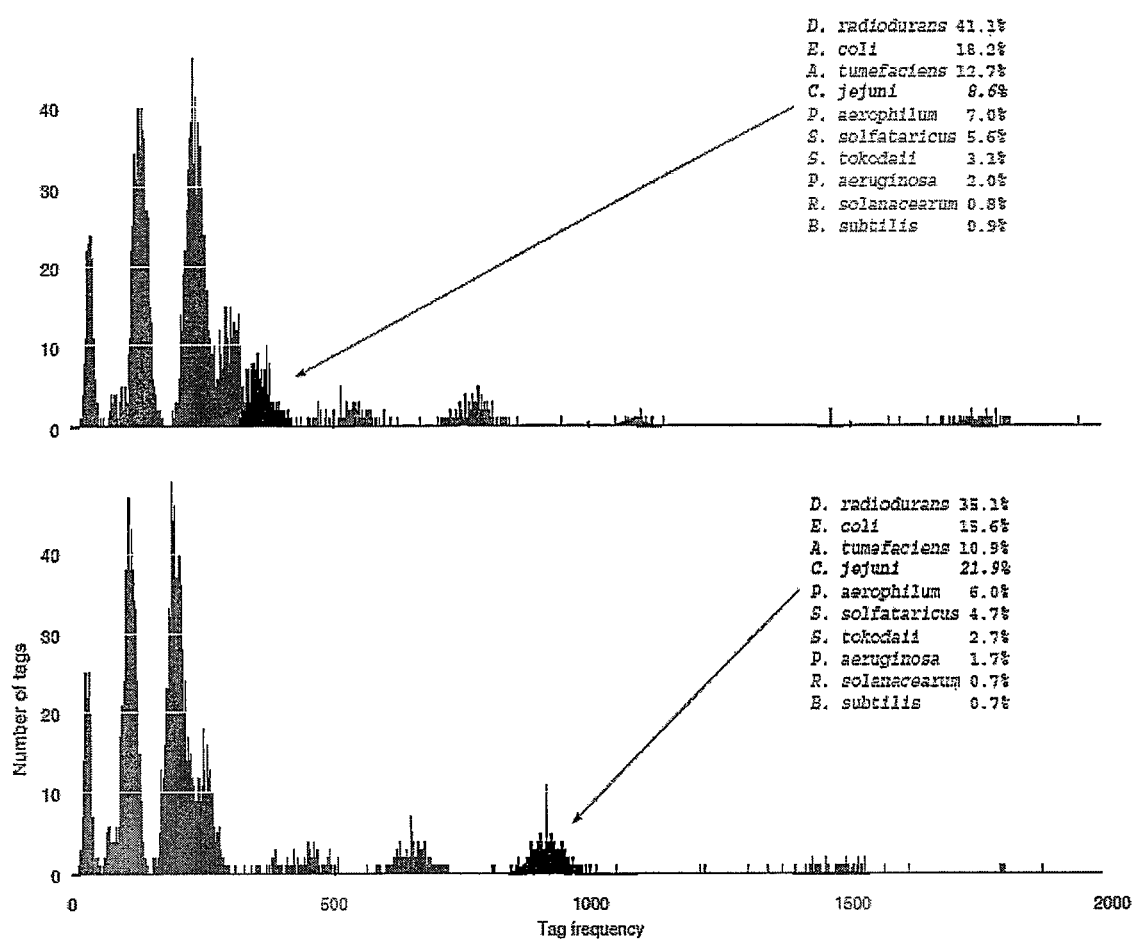
FIG. 4 represents computer simulations of the GSTs of two virtual samples containing ten organisms in which the relative amount of one of the organisms differs significantly between the two samples.

An in silico Monte-Carlo simulation of two randomly generated virtual consortia of ten fully sequenced microbes using SpeI as the fragmenting enzyme, NlaIII as the anchoring enzyme, and MmeI as the tagging enzyme gave the results shown in FIG. 4.

In the two virtual mixtures, the relative abundance of one of the organisms (C. jejuni) was altered and the resultant changes in the distribution of GSTs was readily apparent upon analysis at a depth of 1,000,000. Virtual sequencing to this depth enabled the identification of organisms in the mixtures that were present at less than one percent relative abundance.

Provided biases in isolation of DNA from a complex sample, biases in amplification, and etc. are avoided, the likelihood that a specific tag of an organism will be sampled is determined by a combination of the organism's relative abundance in the mixture and the number of GSTs generated from the organism's DNA by the particular fragmenting and anchoring enzymes chosen for the the analysis. As illustrated in FIG. 4, the frequency distribution of over-sampled tags from a mixture will exhibit peaks of tags, clustered by organism.

Single Point GST

In order to validate the SP-GST procedure outlined in FIG. 3B, Dr. F. Brockman of Pacific Northwest National Laboratory provided Deinococcus radiodurans R1 DNA mixed with the DNAs of four other bacterial species. D. radiodurans DNA was 6.3% of the total DNA of the mixture. The mixture was first fragmented with (G↓TAC). An MmeI-containing duplex linker was ligated to the fragment ends and amplification was carried out using biotinylated anchoring primer "a" of FIG. 3B, the 8-27R microbial 16S rDNA universal primer (e.g., Shashkov, et al. (2002) Eur. J. Biochem 269: 6020-6025) (an alternative is the 8-26 reverse rDNA primer—see Hicks, et al. (1992) Appl. Environ. Microbiol. 58:2158-2163). After capturing the amplified fragments on streptavidin beads, the duplex linker and the appended SP-GSTs were released by MmeI cleavage. The resulting SP-GST library was analyzed by the sequencing methods of the general GST method and the results revealed two different D. radiodurans tags adjacent to the Csp6I sites (A in FIG. 3B) that are known to be next to the 5' terminus of the three 16S gene copies of D. radiodurans. One tag, GTACGGCGCG-GACGCTCTGC (SEQ ID NO: 62), is located in section 198 of chromosome 1 (White, et al. (1999) Science 286:1571-1577) (White, et al. (1999) Science 286:1571-1577) and is 373 bps upstream of the start of the 16S rDNA gene. The second tag, GTACTATTTCTGAGCCTCGA (SEQ ID NO: 63), is located in sections 8 and 213 of chromosome 1 and is 270 bps upstream of the 16S rDNA sequences in the duplicated rDNA operons. Thus, in a complex microbial sample, the SP-GST method, applied to rDNA, could be used successfully to identify species of organisms.

CpG Islands

Two approaches to examining hypermethylated CpG islands in human DNA have been initiated. One makes use of MseI fragmentation followed by isolation of hypermethylated sequences on a histidine-tagged methyl-CpG-binding protein (HMBD—Histidine tagged Methyl Binding Domain) affinity resin (Cross, et al. (1994) Nature Genet. 6:236-44). The other approach makes use of fragmentation with a methyl-sensitive fragmenting enzyme followed by secondary fragmentation using a methyl-insensitive isoschizomer to identify GSTs associated with methyl CpG islands.

For the HMBD approach, recombinant HMBD was produced from the pET6HMBD vector provided by S. H. Cross (see Cross et al., 1994). Transformed E. coli BL21(DE3) were cultured at 20° C. under conditions that provide for auto-induction of T7 RNA polymerase from the bacterial chromosome, and hence, expression of the recombinant protein from the T7 RNA polymerase promoter. Affinity resin is prepared by binding the histidine tagged methyl-binding methyl-binding domain Ni-agarose.

The affinity purification of MseI fragments containing a high density of 5-methyl-CpGs was carried out on genomic DNA from LNCaP, a widely used adult human prostatic epithelial cell line. To ensure complete digestion with the fragmenting enzyme, MseI (there are approximately $37.8 \times 10^6$ MseI recognition sites in the human genome), 10 μg of DNA was cleaved with MseI, phenol extracted, and then cleaved again with MseI. The digest was then passed over the HMBD column, the column was washed to remove non-binding, non-methylated fragments and the fragments that were tightly bound were eluted with high salt and again digested with MseI and rechromatographed.

A duplex linker, having a terminus compatible with the TA overhang produced by MseI and a restriction site for the type IIS endonuclease, MmeI, was ligated to the ends of the methylated fragments. The ligation products were rechromatographed on the affinity matrix to remove excess linkers. Stepwise elution, 0.6M to 0.75M NaCl followed by 0.75M to 1M NaCl, was used to fractionate the linkered methylated fragments into two sets, one more highly methylated, and therefore more tightly bound to the affinity matrix (eluted at 0.75-1M NaCl), than the other.

The fractionated ligation products were then digested with MmeI and the digestion products were again passed over the HMBD column in low salt, so that the duplex linker and its appended signature tag was eluted in the flow-through and therefore separated from the methyl-CpG-rich fragments. The duplex linker-appended signature tags were then ligated with a 16-fold degenerate amplification adapter that adds three consecutive C residues and a second site for MseI. The ligation products were amplified using one primer specific for the duplex linker and the other specific for the amplification adapter.

The sequences of the GSTs that were isolated in this fashion were determined using the concatamerization and cloning methods described above. Software designed to process the concatemerized GSTs and to collect the tags in a relational database, preloaded with human tags (TTAAN$_{17}$) from the April, 2003 frieze of the human genome. High-throughput tag sequence intercomparisons are accomplished through a combination of SQL queries and use a specially designed Smith-Waterman (J. Mol. Biol. 147:195-197 (1981)) comparator that we optimized for rapid comparisons between GST sequences and the NCBI database sequences. Unique hits were then mapped to their respective locations within the human genome and the output presented in both numerical and graphical modes using the BNL-developed software.

Simulations predicted that 77.5% or 29,302,174 of the total 37,794,064 MseI tags in the human genome would map to unique sites prior to any HMBD fractionation. The most highly-abundant MseI abundant MmeI tag in our simulation occurs only 19,222 times. Clearly, the HMBD fractionation could skew these proportions if the method were to select preferentially for Methyl-CpG fragments from repeated sequences.

Shiraishi, et al., (Proc. Natl. Acad. Sci. USA 96:2913-2918 (1999)) reported that a surprisingly high fraction of Tsp5091 (A↓AATTT) derived fragments that bound tightly to HMBD were relatively short, about 200 bp, with a limited number of CpGs and many were derived from Alu sequences. Although the reasons for this bias are unclear, they may include variables such as incomplete re-folding of the recombinant HMBD protein which had been isolated from inclusion bodies, causing some non-specific DNA binding to the HMBD resin or selection during their cloning step.

Our data, which were obtained without having to resort to recovery of the HMBD from inclusion bodies and which did not require cloning of intact CpG islands, are much closer to the expected values (310 unique tags and 108 multiple tags in the 0.6-0.75 M NaCl cut and 250 unique tags and 78 multiple tags in the 0.75-1.0 M NaCl fraction). One such result for a unique tag from the 0.6-0.75 M NaCl fraction localized the MseI-GST sequence: TTAATTCCGATAACGAACGA (SEQ ID NO: 64) to one end of a 1.5 kb MseI fragment from chromosome 12 that spans the 5' portion of the UHRF1 gene, the expression of which is reported to be deregulated in cancer cells (Mousli, et al. (2003) Brit. J. Cancer 89:120-127). Cancer 89:120-127).

Using the approach of identifying tags adjacent to methylated SmaI recognition sequences, DNA from the LNCaP cell line was first digested with SmaI, which blunt end cuts at non-methylated sites, and then digested with its methyl-insensitive isoschizomer, XmaI, thereby yielding fragments having either two blunt ends, one blunt end and one XmaI overhang end, or two XmaI overhang ends. The fragments having at least one XmaI overhang were then ligated to a biotinylated capture adapter having one terminus compatible with the 4 base-XmaI overhang. The ligation products were then digested to completion with MseI as the anchoring enzyme and captured on streptavidin beads. The captured digestion products were ligated to the duplex linker used in the HMBD procedure (having a terminus compatible with the TA MseI overhang and a restriction site for MmeI). The bound ligation products were then digested with MmeI to release the duplex linker and the appended tags. The released duplex linker—tag fragments were then ligated to the degenerate amplification adapter of the HMBD procedure, and after amplification the GSTs were sequenced.

From the current sequence of the human genome we have determined that there are 603,200 potential MseI sites adjacent to SmaI (XmaI) sites which would generate a total of 530,727 distinct GSTs. Of these, 84% (506,145) occur at unique positions in the in the human genome. The SmaI/XmaI GST library is currently being sequenced. Preliminary results indicate that most tags can be uniquely mapped to identify their corresponding position in the latest frieze of the genome. As an example, the tag TTAAACAGTTGGGCTGCGCT (SEQ ID NO: 65) maps on chromosome 9 in a 1.6 kb MseI CpG island that spans the beginning of the transcriptional start of a homeobox transcription factor (see FIG. 5).

Figure 5:
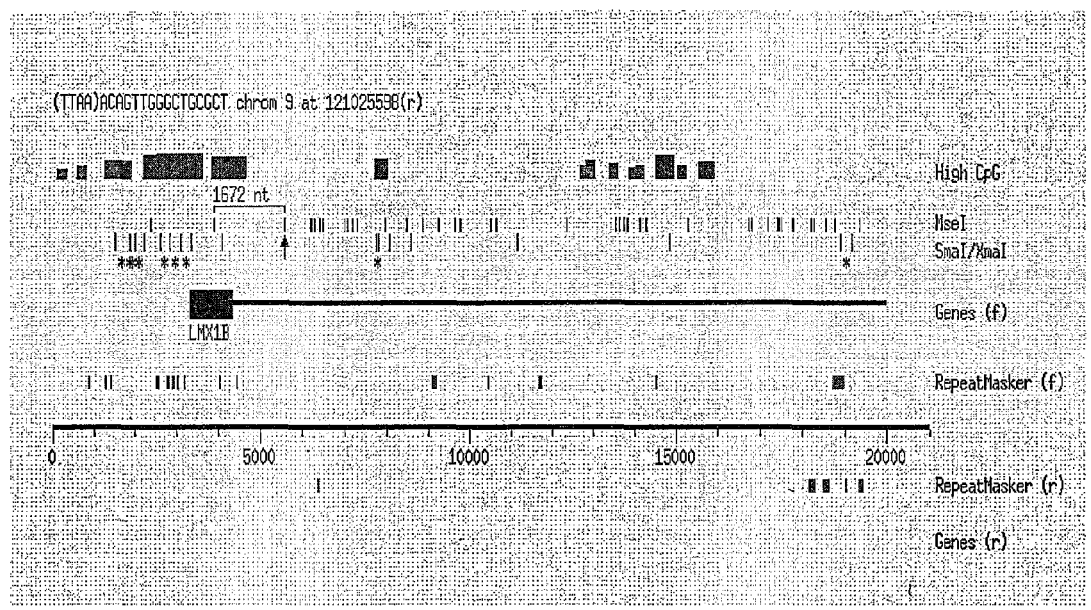
FIG. 5 shows a 20 kb DNA segment containing a methyl-CpG SmaI site in the CpG island near the start of a homeobox transcription factor on chromosome 9. The methyl-CpG-associated tag location is shown by the arrow.

As indicated in FIG. 5, in some of the CpG islands there are two or more SmaI sites without an intervening MseI site (marked by asterisks in FIG. 5). This method would fail to extract tags from these internal SmaI site(s) if they were methylated. Scanning the human genome sequence revealed there are 11,946 clusters of 2 or more contiguous SmaI (XmaI) fragments. Over half of the MseI-less fragments are in contiguous clusters of two or more SmaI (XmaI) sites, or about 10% of the 370,023 SmaI (XmaI) fragments in the genome. GSTs can be obtained from these sites, either individually or from pairs of adjacent methylated SmaI site pairs by ligating the XmaI-cut DNA with a cassette containing an MmeI recognition sequence immediately adjacent to the XmaI overhang. If the XmaI overhang is retained for cloning purposes, the GSTs will be CGGG+15 nucleotides. Only 46% of these tags would be unique primarily due to a preponderance of tags from Alu sequences. With the high-throughput nature of the high-throughput nature of the downstream sequencing steps, this may not be too great a penalty to pay for global profiling.

GST METHODS

General GST Procedure
DNA Fragmentation and Biotinylated Capture Adapter Ligation DNA from avirulent *Yersinia pestis* EV766, a $Ca^{2+}$ independent strain cured of the 70.5 kb pCD1 plasmid but retaining the pPCP1 9.5 kb and 100 kb pMT1 plasmids (Portnoy et al., (1981) J Bacteriol 148:877-83), was kindly provided by James Bliska, State University of New York (SUNY) at Stony Brook (SB). Ten micrograms was digested with 100 U of BamHI (New England Biolabs (NEB), Beverly, Mass.), extracted with an equal volume of phenol/chloroform (P/C), and precipitated with ethanol. After centrifugation, the pellet was resuspended in 34 μl TEs1 (10 mM Tris-HCl, pH 8.0, 0.1 mM EDTA-$Na_3$). A biotinylated GATC oligonucleotide capture adapter was created by mixing 3600 pmol each of two synthetic oligonucleotides (sense strand: CGA ACC CCT TCG (SEQ ID NO: 1); antisense strand: P-GAT CCG AAG GGG TTC GT-Biotin (SEQ ID NO: 2) in 100 μl OPA buffer (10 mM Tris-acetate, pH 7.5, 10 mM Mg acetate, 50 mM K acetate, Amersham Bioscience, Piscataway, N.J.) heating them to 95° C. for 2 min and then allowing them to cool slowly to room temperature. An approximate 50-fold excess of biotinylated adapter (~600 pmol), relative to available BamHI ends, was ligated to the fragmented DNA in a total volume of 50 μl of 50 μl of 1× ligase buffer containing 350 U of T4 DNA ligase (Takara, Shiga, Japan). The reaction was incubated overnight at 16° C. followed by extraction with an equal volume of P/C. The sample was precipitated with ethanol, centrifuged and resuspended in 83 μl TEs1.

First Digestion with NlaIII and Binding to Magnetic Beads

The fragmented DNA was next digested with 25 U of NlaIII (NEB) in 100 μl NlaIII digestion buffer (1×NEB buffer #4 supplemented with 1×BSA and 10 mM spermidine-HCl) for 3 hours at 37° C.; NlaIII digestion is stimulated 2 to 4-fold by addition of spermidine (unpublished observations). One hundred μl (1 mg) of streptavidin magnetic beads (Dynal Biotech. Inc., Lake Success, N.Y.) were washed twice with 200 μl of 1× magnetic bead binding buffer (MBB: 10 mM Tris-HCl, pH 7.4, 1 mM EDTA-$Na_3$, 1 M NaCl), and then resuspended in 100 μl of 2×MBB. The beads were then added to the NlaIII digested DNA in a non-stick 1.5 ml microfuge tube (Ambion, Austin, Tex.). The beads and digest were mixed gently for 1 hour at room temperature to bind biotinylated BamHI-NlaIII fragments.

Second Digestion with NlaIII and MmeI Duplex Linker Ligation

A second incubation with NlaIII was performed on the bound fragments by resuspending the beads in 200 μl NlaIII digestion buffer containing 25 U of enzyme and incubating for 2 hours at 37° C. The beads were washed three times with 200 μl TEs1 to remove non-bound DNA fragments and one time with 200 μl 1× T4 ligase buffer. An MmeI oligonucleotide linker (i.e. the duplex linker) was created by mixing and annealing, as described above, 1000 pmol each of two synthetic oligonucleotides (sense strand: TTT GGA TTT GCT GGT CGA GTA CAA CTA GGC TTA ATC CGA CAT G (SEQ ID NO: 3); antisense strand: P-TCG GAT TAA GCC TAG TTG TAC TCG ACC AGC AAA TCC-(AmMC7) (SEQ ID NO: 4)) in 100 μl 1×OPA. The annealed duplex linker (40 pmol) was ligated to the fragmented solid-phase DNA for 2 hours at 16° C. in a total volume of 50 of 1× ligase buffer containing 350 U of T4. DNA ligase.

Digestion with MmeI

Beads were washed six times with 400 μl 1×MBB and then washed several times with 200 μl MmeI digestion buffer (100 mM HEPES, pH 8.0, 25 mM K acetate, pH 8.0, 50 mM Mg acetate, pH 8.0, 20 mM DTT, 4 mM S-adenosylomethionine-HCl). The beads were then resuspended in 100 μl 1× MmeI digestion buffer containing 8 U MmeI (Center of Technology Transfer, Gdansk, Poland, and, more recently, NEB) and incubated for 2 hours at 37° C. with occasional mixing. The beads were collected and the supernatant containing the released tags was removed to a clean microfuge tube. The beads were washed with 100 μl TEs1 and the wash combined with the first MmeI supernatant. The pooled MmeI digest is extracted with an equal volume of P/C and precipitated at −80° C. for 1-2 hours with 1 ml of ethanol after addition of 133 μl 7.5 M ammonium acetate and 2 μl Glyco Blue (Ambion) as carrier. The resulting pellet was washed with cold 75% ethanol, dried in vacuo and resuspended in 29.5 μl TEs1 plus 4 μl 10× T4 DNA ligase buffer.

Amplification Adapter Ligation and Initial PCR Amplification

A 16-fold degenerate adapter cassette (i.e. the amplification adapter) was prepared by annealing two synthetic oligonucleotides as described above (sense strand: pTTC ATG GCG GAG ACG TCC GCC ACT AGT GTC GCA ACT GAC TA-AmMC7 (SEQ ID NO: 5); antisense strand: TAG TCA GTT GCG ACA CTA GTG GCG GAC GTC TCC GCC. ATG AAN N (SEQ ID NO: 6)). Thirty-five pmol of amplification adapter (3.5 μl) was added to the resuspended tags, and after 15 min at room temperature, 3 μl of ligase (1000 U) (Takara) was added and the reaction incubated overnight at 16° C. The ligation products were subjected to PCR amplification consisting of an initial denaturation step at 95° C. for 2 min followed by 30 cycles of 95° C. for 30 s, 58° C. for 30 s and 72° C. for 30 s with a final extension step at 72° C. for 4 m using 5'-Biotin-GGA TTT GCT GGT CGA GTA CA (SEQ ID NO: 7) and 5'-Biotin-TAG TCA GTT GCG ACA CTA GTG GC (SEQ ID NO: 8) as forward and reverse primers, respectively, each respectively, each at a final concentration of 0.4 μM. Cycling was performed in 1× Promega buffer containing 3 mM Mg sulfate and 20 pM of each dNTP. Typically, 1.0 μl of ligation product was amplified in a 200 μl reaction containing 0.1 μl Platinum Taq DNA polymerase mixture (Invitrogen, Carlsbad, Calif.). It should be noted that the amplification adapter was designed to add two consecutive T residues and a second anchoring enzyme (e.g. NlaIII) site on the ends of the original MmeI generated fragments (TTCATG . . . ). Such a design is optional according to the present invention. Inclusion of such a feature, however, can add versatility to the protocol because 1) each tag will be clonable via termini generated by a common anchoring enzyme (e.g. NlaIII) and 2) the two T/A base-pairs donated by the degenerate linker can help stabilize the identifier portion of the tag.

Linear Amplification to Reduce Heterogeneity (Heteroduplex Formation) (LARHD)

The PCR products were then subjected to one round of linear amplification to reduce heterozygosity (LARHD) by diluting them to 1 ml with 800 µl 1× PCR buffer containing 4 µl Platinum Taq and 400 pmol of each Biotinylated primer. The reaction was then incubated at 95° C. for 2.5 m, 58° C. for 30 s, and 72° C. for 5 m. Unincorporated primers were digested by addition of 10 µl (200 U) of single-strand specific E. coli Exo I. After one hour at 37° C. the sample was P/C the sample was P/C extracted and precipitated by addition of 2.5 volumes of ethanol in the presence of 0.3 M sodium acetate, pH 6.0.

Second Linear amplification (LARHD2), NlaIII Digestion and Concatemerization

Following centrifugation, the pellet was washed in 70% ethanol, dried and then dissolved in 200 µl TEs1. A portion (20%) was subjected to 25 additional rounds of linear amplification under the above LARHD conditions, except only the forward primer was added. This was then followed by one round of amplification after addition of the reverse primer and additional DNA polymerase to convert the linear amplification products to double-stranded DNA. Typically, 1 ml of sample is amplified and any unincorporated primers are hydrolyzed by incubation with Exo I as above. After P/C extraction and ethanol precipitation, the amplified DNA is digested with 20 U of NlaIII in 400 µl at 37° C. for 4 hours (after 2 h the completion of digestion is checked by electrophoresis of a small aliquot on a 10% polyacrylamide gel). The digest is then extracted on ice with chilled P/C to prevent denaturation of the smaller GSTs and ethanol precipitated from Na acetate in the presence of Glyco Blue carrier. The sample is chilled for several hours and then centrifuged at 4° C. The pellets are resuspended in 200 µl ice cold TEs1 plus 25 mM NaCl, diluted diluted with an equal volume of 2×MBB and added to 200 µl (2 mg) of streptavidin beads equilibrated with 1×MBB. After gentle mixing for 15 m at room temperature, the unbound fraction is transferred to a second 200 µl aliquot of beads to capture any remaining biotinylated DNA fragments. The unbound GST fraction is recovered and precipitated by addition of 2.5 volume of ethanol and Glyco Blue, carrier and concatemerized with T4 DNA ligase (5 U/µl, Invitrogen) at 16° C. for 6 hours. The sample was subjected to electrophoresis on a 0.75% low melt agarose gel and products greater than 100 bp were recovered. These products were cloned into the SphI-site of a pZero plasmid (Invitrogen) that was engineered to have a SphI-minus KanR gene (unpublished). Recombinant clones obtained after electroporation of competent TOP10 cells (Invitrogen) are selected on 2×YT plates containing 50 µg/ml kanamycin. A schematic representation of the method is shown in FIG. 1 and a complete description of all steps is available at the web site (http://genome.bnl.gov/GSTs/).

DNA Sequencing

Plasmid DNA for sequencing was prepared using Edge BioSystems (Gaithersburg, Md.) reagents and protocols in 96-well plates. Templates were cycle sequenced using ABI Prism BigDye® terminator chemistry from the M13 forward primer and analyzed on ABI 3700 sequencers. Extracted data were ported to an Oracle® database and searched for valid tags using the GST software. The software ensures that only unambiguous 21-22 bp tag sequences, see below, are extracted for further analysis (tags with Ns, lengths other than 21-22 bases or whose polarity is unambiguous), are extracted to separate files for manual editing or further examination.

Ligation-Mediated PCR

The following five Y. pestis-specific GSTs were synthesized for use as primers: [535,384] CAT GCA GGG TGC ACG ACC CGA (205R) (SEQ ID NO: 9); [2,281,342] CAT GTG GCC GCC GCG CTT AA (384R) (SEQ ID NO: 10); [2,894,318] CAT GAC TCT GCC ATA GCT TCG (1031R) (SEQ ID NO: 11); [3,452,611] CAT GCA GGA CCG CGG ACA ATG (102F) (SEQ ID NO: 12); and [4,145,945] CAT GCA GTG CCA TCC TCA CGG (230F) (SEQ ID NO: 13). The values in brackets are the position of the NlaIII tagging site in the *Y. pestis*. chromosome. The values in parentheses are the distances between the respective NlaIII and BamHI sites, and the directionality of the PCR reaction. BamHI digested *Y. pestis* DNA was ligated with a non-biotinylated GATC oligonucleotide adapter created by mixing and annealing 3600 pmol each of two synthetic oligonucleotides (sense strand: CGT AAT ACG ACT CAC TAT AGG GA (SEQ ID NO: 60); antisense strand: GAT CTC CCT ATA GTG AGT CGT ATT ACG (SEQ ID NO: 61)) in 100 μl OPA, as described above. The annealed GATC adapter (40 pmol) was ligated to BamHI fragmented DNA for 2 hours at 16° C. in a total volume of 50 at 16° C. in a total volume of 50 μl of 1× ligase buffer containing 350 U of T4 DNA ligase (Takara). Aliquots of the Tinkered DNA were incubated at 94° C. for 2 min, followed by 10 rounds of linear amplification (94° C. for 20 s, 55° C. for 30 s and 68° C. for 4 min) with the above *Y. pestis*-specific primers. This was followed by 25 additional rounds of amplification under the same conditions after addition of the common GATC-specific primer, the GATC sense strand. Products were extended for 10 m at 68° C. and analyzed on polyacrylamide gels. Extension with the sense strand primer should add an additional 23 bp to the BamHI end of all the amplification products.

rDNA SP-GST Methods for Microbial Analysis of Soil Samples

Fragmentation

After isolation and verification of the quality of the DNA isolated from a soil sample, 5 μg of DNA in 100 μl was digested with 20 units of the fragmenting enzyme, Csp6I (G↓TAC) (Fermentas, Vilnius, Lithuania), in Fermentas 1× B+ buffer plus 1× bovine serum albumin (BSA) for 2 hours at 37° C. The enzyme is inactivated by heating the mixture to 65° C. for 20 min. and the digested DNA was then purified on a GFX column (Amersham) according to the manufacturer's instructions.

Ligation of the Csp6I Partially Duplex Linker

A partially duplex linker having a cohesive terminus compatible with the TA overhangs produced by Csp6I and containing a restriction site for MmeI was ligated to the purified digested DNA. The partially duplex linker was formed by annealing TTT GGA TTT GCT GGT CGA ATT CAA CTA GGC TTA ATC CGA CG (SEQ ID NO: 66) and dephosphorylated TAC GTC GGA TTA AGC CTA GTT GAA TT (SEQ ID NO: 67). Ligation was carried out at 16° C., overnight, in a total volume of 50 μl using an approximately 50-fold excess of the partially duplex linker, 3 μl of T4 DNA ligase in 1× T4 DNA ligase buffer (Takara). The ligation products were purified on a GFX column as above.

Linear Amplification of 16S rDNA and Upstream Sequences

The anchoring primer (the reverse 8-27 16S rDNA primer), Biotin-CTG AGC CAG GAT CAA ACT CT (SEQ ID NO: 68), was then used to linearly amplify only those ligation products that carry the 5' terminus of microbial 16S rDNA. In a reaction volume of 50 μl, using Taq polymerase, the reaction mixture was subjected to 35 rounds of linear amplification with the following steps: 95° C., 2 min; 35 rounds of 95° C.

for 30 seconds, 52° C. 30 seconds and 72° C. for 3 minutes; concluded by incubation at 72° C. for 8 minutes and then holding at 4° C.

PCR Amplification

In the foregoing, the ligation products that were not amplified because they lack rDNA sequences continue to be flanked by linkers having single stranded 5' termini. In contrast, the single stranded products of the linear amplification are the only DNA fragments in the mixture having 3' ends complementary to the single stranded portion of the partially duplex linker and therefore are the only fragments that can be amplified by PCR amplification using the anchoring primer (SEQ ID NO: 68, above) in combination with the second primer—GGA TTT GCT GGT CGA ATT CAA C (SEQ ID NO: 69). An aliquot of the linear amplification product mixture was PCR amplified using SEQ ID NO: 68 and SEQ ID NO: 69 as primers in 50 µl using the same temperature cycles as for the linear amplification procedure.

Capture and Digestion with MmeI

The PCR amplified products were then captured on magnetic streptavidin beads as described in the general GST procedure. Unbound DNA was removed by washing the beads three times with binding buffer and twice with TE (50 mM Tris HCl, pH 8, 0.1 mM EDTA) and once with restriction Buffer #4 (NEB). The beads are then collected and the supernatant carefully removed and replaced with 100 µl of MmeI digestion reaction mixture consisting of 1× restriction Buffer #↓BSA, 40 µM S-adenosylmethionine and 20 units of MmeI. The suspension was incubated for 1.5 hours at 37° C. with 37° C. with occasional mixing. An additional 20 units of MmeI was added and the suspension incubated for an additional 1.5 hours at 37° C.

After digestion, the fully duplex linker and appended 16S rDNA SP-GSTs were released from the beads into the supernatant after collection of the beads. The linker and appended SP-GSTs have the following structure, comprising SEQ ID No: 70 (top strand) and its-complement, SEQ ID NO: 71 (bottom strand):

```
5'-GGATTTGCTGGTCGAATTCAACTAGGCTTAATCCGACGTAC(N)₁₅NN       (SEQ ID NO: 70)
   CCTAAACGACCAGCTTAAGTTGATCCGAATTAGGCTGCATG(N')₁₅-5'.    (SEQ ID NO: 71)
```

The underlined sequence represents the MmeI recognition sequence and the sequence in italics is the reconstituted Csp6I recognition sequence. The released tags and appended linkers were purified by phenol/chloroform extraction and ethanol precipitation.

The purified SP-GSTs and appended tags were ligated to a degenerate amplification adapter formed by annealing 5'-TTT GTA CGG CGG AGA CGT CCG CCA CTA GTG TCG CAA CTG ACT A (SEQ ID NO: 72) its degenerate complement 5'-T AGT CAG TTG CGA CAC TAG TGG CGG ACG TCT CCG CCG TAC AAA NN (SEQ ID NO: 73) where the sequence in italics is the recognition sequence for Csp6I so that the 16S SP-GSTs are flanked by a linker and an adapter, each having a Csp6I recognition site. After ligation overnight at 16° C., the ligation products were amplified using a pair of primers, one specific for the duplex linker and the other specific for the amplification adapter. The primer specific for the duplex linker is 5'-Biotin-GGA TTT GCT GGT CGA ATT CA (SEQ ID NO: 74) and the primer specific for the amplification adapter is 5'-Biotin-TAG TCA GTT GCG ACA CTA GTG GC (SEQ ID NO: 75). The amplification is carried out for 30 cycles comprising melting at 95° C. for 30 seconds, annealing at 58° C. for 30 seconds and elongation at 72° C. for 30 seconds. Heteroduplexes are resolved by rounds of linear amplification as described in the general GST methods.

After amplification sequences were determined as described in the general GST method.

Methods and Materials for Methyl-CpG Island-Associated GSTs

MseI Fragmentation Method

Expression of HMBD

HMBD, the recombinant histidine-tagged methyl-CpG binding domain (HMBD) has been obtained by others using 37° C. IPTG induction of cultures containing the T7-based expression plasmid, pET6HMBD (Cross et al., 1994), a plasmid which places the HMBD target under control of a hybrid T7/Lac promoter (Studier et al. (1990) Methods Enzymol 185:60-89). The induced protein, which forms inclusion bodies, is purified from the bacterial extracts by cation exchange under denaturing conditions (5M urea) and then refolded by refolded by dialysis against renaturation buffer or by buffer exchange after it is coupled to Ni-agarose.

Recently, F. W. Studier has found that IPTG induction is not needed to turn on expression of the gene for T7 RNA polymerase in BL21(DE3) (U.S. patent application Ser. No. 10/675,936, filed Sep. 30, 2003). By growing cells in the presence of a mixture of glucose, glycerol and lactose, transcription from the lac operon, and therefore, expression of the T7 RNA polymerase, is at first repressed since glucose is initially used as the preferred carbon source. As glucose is exhausted, the cells begin to utilize glycerol. As the glycerol is in turn exhausted the cells switch to utilization of lactose and the lac operon becomes maximally induced and the T7 RNA polymerase is expressed as if the cells had been induced with IPTG. The only important requirement for the use of this methodology is that the cells be competent for growth on lactose which is the case for BL21(DE3).

We have tried this system with pET6HMBD and found that auto-induction at 20° C. for 24 hr reproducibly yields about 30-40 mg of soluble HMBD protein per 100 ml culture after chromatography of the soluble fraction on SP Sepharose Fast Flow, which is more than, enough to prepare 1-2 ml of the affinity resin. Auto-induction at 37° C. yields the same amount of HMBD protein; however, it is all insoluble.

Expression of soluble HMBD by auto-induction at 20° C. is followed by cell lysis and metal chelate chromatography. Three hundred to 400 mg of electrophoretically homogeneous protein can be obtained from a liter of induced cells. Renaturation is not required, helping to ensure protein uniformity from preparation to preparation.

Affinity Resin Preparation

Coupling of the affinity purified HMBD protein to Ni-agarose resin was done with slow stirring at 4° C. for 30 min. A standard ratio used to prepare the affinity resin is 25 mg of protein to 1 ml of Ni-NTA-agarose resin (Qiagen, Valencia, Calif.) in buffer described by Cross et al. (1994). The charged resin is then poured into a suitable column and washed with 4 volumes of buffer to elute unbound material. The amount of uncoupled HMBD protein in the pooled flow-through and wash is determined by the Bradford assay (Anal Biochem 72:248-54 (1976)) and SDS polyacrylamide gel electrophoresis (PAGE) to determine the efficiency of coupling with is typically >95%. The coupled resin is extruded from the column and stored at 4° C. in the presence of a cocktail of protease inhibitors. Under these conditions, the HMBD affinity resin appears to be stable for a least 6 months. Aliquots (1 ml) are removed as needed to prepare columns for DNA fractionation. Since the amount of HMBD coupled to the Ni-agarose determines to some extent the NaCl concentration at which differentially methylated differentially methylated DNAs elute (Cross et al., 1994), we believe that careful attention to protein preparation and its coupling to the support are important for standardizing HMBD chromatography.

Calibration

Each HMBD column preparation was tested for its CpG island binding properties using the method of Shiraishi, et al. (1999). Fragments of restriction digested phage T7 DNA with known amounts of CpGs are modified by SssI methyltransferase (for full methylation) or HpaI methyltransferase (for partial methylation) and their methylation status determined by resistance to digestion with HhaI and HpaII. At least three differently sized fragments of each type (non-methylated, partially and fully methylated—i.e., a pool of 9 total fragments) are prepared and their HMBD elution profiles determined by Southern hybridization using the corresponding fragments as probes after stepwise elution with increasing concentrations of NaCl. Fragments are loaded in 0.4M NaCl, a condition under which unmethylated DNA flows through the column. The bound fragments are eluted in 0.1 ml aliquots of buffer containing 40 mM incremental increased in NaCl concentration, from 0.44M to 1.0M.

MseI Digestion and Fractionation of DNA

Human genomic DNA (10 μg) from LNCaP, a widely used adult human prostatic epithelial cell line, was digested twice the MseI and then fractionated by HMBD chromatography. Fractions eluting between 0.5M and 1M NaCl were collected, precipitated with ethanol and then redigested with MseI to ensure their complete digestion. The DNA was then rechromatographed as before to generate the total Methyl-CpG fraction. Stepwise elution: (a) 0.5-0.65M NaCl; (b) 0.65-0.85M NaCl; and (c) 0.85-1.0M NaCl is used to separate the fragmented DNA into fractions having increasing levels of methylated CpG sequences. Each fraction was then rechromatographed and eluted at its original salt concentration.

Library Construction

Each eluted pool (a, b, and c) was ligated with an excess of a duplex linker MmeI-MseI cassette prepared by annealing of 5'-TTT GGA TTT GCT GGT CGA GTA CAA CTA GGC TAA TCC GAC T (SEQ ID NO: 76) and 5'-TAA GTC GGA TTA GCC TAG TTG TAC TCG ACC AGC AAA TCC (SEQ ID NO: 77) where the MmeI recognition site is underlined. The linkered fragments are rechromatographed on the HMBD column and then cleaved with MmeI as for capture adapter-bound linkered fragments of the general GST protocol. The duplex linkers and appended methyl-CpG-associated GSTs were recovered in the flow through after cleavage.

The released duplex linkers and appended GSTs were ligated to a degenerate amplification adapter prepared by annealing of 5'-pCCC TTA AGC GGA GAC GTC CGC CAC TAG TGT CGC AAC TGA CTA (SEQ ID ID NO: 78) and 5'-TAG TCA GTT GCG ACA CTA GTG GCG GAC GTC TCC GCT AAG GGC NN (SEQ ID NO: 79).

The GSTs associated with methyl-CpG islands, flanked by the duplex linker and the amplification adapter were amplified by PCR using biotinylated primers, one specific for the amplification adapter and the other specific for the duplex linker.

The amplified fragments were cleaved with MseI to release the GSTs with three appended G:C base pairs. The two biotinylated end fragments were separated from the released GSTs by binding them to streptavidin beads. The purified tag fragments were ligated together to form random concatemers. Minimal length (approx. 500 bp) concatemers were isolated from agarose gels, cloned into NdeI-cut (CA↓TATG) pGEM5 (Promega, Madison, Wis.) to create a methyl-CpG island library from the cells.

Library Sequencing

The cloned concatemers were sequenced to establish a database of methyl-CpG island-associated GSTs from the genomic DNA of the human prostate epithelial cells. This database can now be compared to results obtained from DNA isolated from cells of various origin or following various treatments of cells, etc., to illustrate methylation changes between cell types, cell health, physiological state, etc.

SmaI (XmaI) Methyl-CpG Island-Associated GST Methods

Sequential Digestion with Two Fragmenting Enzymes.

Human genomic DNA from LNCaP cells was digested to completion with SmaI, and then purified by phenol/chloroform extraction and ethanol precipitation. The fragmented DNA was then digested to completion with XmaI and purified.

Ligation with Capture Adapter, Digestion with MseI Anchoring Enzyme and Capture.

A biotinylated capture adapter, having one terminus compatible with the XmaI overhang was ligated to the fragmented DNA as in the general GST protocol. The ligated fragments are then digested with MmeI and captured on streptavidin beads. The captured fragments were redigested with MseI to ensure complete digestion.

Duplex Linker Ligation and GST Release.

The bound digested fragments were ligated with the MmeI-MseI duplex linker (SEQ ID NO: 76 and SEQ ID NO: 77) of the MseI fragmentation method for methyl-CpG Island GSTs. The GSTs and appended duplex linkers were then released from the streptavidin beads by digestion with MmeI.

Amplification Adapter Ligation, Amplification, and Sequencing.

The amplification adapter (SEQ ID NO: 78 and SEQ ID NO: 79) of the MseI fragmentation method was ligated to the GSTs-duplex linker fragments and the flanked GSTs are amplified as above. The above. The amplified GSTs were released by digestion with MseI as above, and the fragment sequences determined.

Methods for Fragmented DNA

Blunt Ending DNA Fragments

DNA fragments were produced by sonication after in vivo crosslinking of DNA binding proteins to the DNA (see Ren et al. (1990) Science 290:2306-2309). After immunoprecipitation to isolate DNA fragments bound to specific binding protein(s) and reversal of the crosslinking as in Ren et al. (2000), the isolated DNA fragments are blunt ended using the DNA Terminator® End Repair Kit from Lucigen® Corporation (Middleton, Wis.). After incubating the fragments of DNA with the kit reagents as suggested by the manufacturer, the blunt ended fragments are purified by phenol/chloroform extraction and ethanol precipitation.

Fragment End DNA Tags Methods ($F_eD$-GST Methods)

Ligation with a Partially Duplex Linker

A partially duplex linker of the following structure:

```
5'-TCCGGTCTACTGAATTCCGAACCGAGGAGGGCCCATCCGAC    (SEQ ID NO: 80)

(dephosphorylated)    CCGGGTAGGCTG-5',  (SEQ ID NO: 81)
``` where the sequence in italics is the recognition site for the type IIS enzyme, BseRI, the underlined sequence is the recognition site for EcoO109I and the sequence in bold typeface is the recognition site for the type IIS enzyme, MmeI, is ligated to to the blunt ended DNA fragments using temperature-cycle ligation (Lund, et al. (1996) Nucl. Acids Res. 24:800-801) overnight, cycling between 30 seconds at 10° C. and 30 seconds at 30° C.

At the end of the ligation the unligated strand (dephosphorylated SEQ ID NO: 81) is melted from the duplex and the DNA fragments ligated to the single stranded linker sequence at the 5' termini are purified on a GFX column.

Duplex Formation and Cutting with MmeI

The ligation products are made fully duplex by filling in the recessed 3' ends using Taq polymerase and dNTPs.

The ligation products are PCR amplified using a biotinylated primer—Biotin-TCC GGT CTA CTG AAT TCC GAA C (SEQ ID NO: 82) and the reaction mixture is then treated with Exonuclease I to remove excess primers. The amplified fragments are then purified by phenol/chloroform extraction and ethanol precipitation.

The purified fragments, flanked by fully duplex linkers, are then digested with MmeI to separate the duplex linkers and their appended fragmented DNA tags ($F_eD$-GSTs) from the internal intervening DNA sequences. After capturing on streptavidin beads the linkers and appended $F_eD$-GSTs are released from the streptavidin and purified by phenol/chloroform extraction and ethanol precipitation.

Ligation with Degenerate Y-Shaped NlaIII Amplification Adapter

A Y-shaped (see Prashar, et al. (1996) Proc. Natl. Acad. Sci. USA 93:659-663) degenerate NlaIII amplification adapter is ligated by overnight thermal cycle ligation to the degenerate ends produced by MmeI. The degenerate Y-shaped amplification adapter is prepared by annealing 5'-pCATGAC GCT ACG TCC GTG TTG TCG GTC CTG (SEQ ID NO: 83) and 5'-ACT ACG CAC CGG ACG AGA CGT AGC GTCATGNN (SEQ ID NO: 84) where the underlined sequence is the recognition sequence for NlaIII and the sequence in bold typeface is the sequence of the primer to be used in the amplification step which follows.

Amplification

The ligation products from the previous step, having the $F_eD$-GSTs flanked by the fully duplex linker and the Y-shaped NlaIII adapter is then amplified using a biotinylated primer specific for the duplex linker:

Biotin-TCC GGT CTA CTG AAT TCC GAA C (SEQ ID NO: 85) and a primer specific for one arm of the Y-shaped adapter:

ACT ACG CAC CGG ACG AGA CGT (SEQ ID NO: 86).

The amplified DNA fragments are purified by phenol/chloroform extraction and ethanol precipitation.

Digestion with NlaIII and Capture

The purified amplification products are digested with NlaIII as described previously and the released duplex linkers and and appended $F_eD$-GSTs and NlaIII overhang are captured on streptavidin magnetic beads.

Sequencing.

The captured products can be sequenced using pyrophosphate sequencing or capillary electrophoresis as described above. Alternatively the NlaIII overhang-terminated $F_eD$-GST can be cleaved from the duplex linker using either EcoO109I or BseRI. The released $F_eD$-GSTs can then be concatemerized, cloned and then sequenced as described in the general GST method.

Fragment Internal DNA Tags Methods ($F_iD$-GST Methods):
Ligation with a Partially Duplex Capture Adapter A partially duplex capture adapter formed by annealing Biotin—TCC GGT CTA CTG AAT TCC GAA CCC CTT GCG GCC GC (SEQ ID: 87) with dephosphorylated 5'-GCG GCC GCA AGG GG (SEQ ID NO: 88) is blunt end ligated to the blunt ended fragments using temperature cycle ligation (Lund, et al, (1996)). Note that the preferred capture adapter has a NotI (or other 8-base cutter) recognition site located at the blunt duplex end. The preferred adapter further lacks recognition sequences for enzymes that are useful as anchoring or tagging enzymes (i.e., lacks sites for MseI, Sau3A, NlaIII, etc. and lacks a site for MmeI). After ligation the covalently ligated product is separated from the non-covalently ligated 14-mer (SEQ ID NO: 88) and any excess adapter by GFX chromatography.

The purified ligation products are made fully duplex by filling in the recessed 3' ends with Taq polymerase and dNTPs.

Amplification

Where necessary, the purified fully duplex ligation products are then amplified using the biotinylated primer: Biotin—TCC GGT CTA CTG AAT TCC GAA C (SEQ ID NO: 89).

Digestion with Anchoring Enzyme and Capture

The fully duplex ligation products or the amplified duplex ligation products are then digested with NlaIII as for the standard GST protocol. The digestion mixture is then contacted with streptavidin beads to capture the fragments attached to the capture adapter. The captured fragments are re-exposed to NlaIII to ensure complete digestion.

Duplex Linker Ligation and MmeI Digestion

A duplex MmeI—NalIII linker prepared by annealing 5'-TTT GGA TTT GCT GGT CGA GTA CAA CTA GGC TTA ATC CGA CATG (SEQ ID NO: 90) with 5'-pTCG GAT TAA GCC TAG TTG TAC TCG ACC AGC AAA TCC (SEQ ID NO: 91) is ligated to the captured digestion products. Note, the MmeI recognition sequence is in bold typeface and the overlapping NlaIII site is in italics. After washing the beads/ the duplex linker and appended $F_iD$-GSTs are released from the column by digestion with MmeI.

Ligation with Degenerate Y-Shaped Amplification Adapter

A Y-shaped degenerate amplification adapter formed by annealing 5'-pTTT CAT GGC GGA GAC GTC CGC CAC TAG TGT CGC AAC TGA CTA (SEQ ID NO: 92) and 5' pNNA AAG TAC CGC CTC TGC AGG CTG TAG ATG CAC TCG AGC TTG C (SEQ ID NO: 93) is ligated to the appended tag—duplex linker fragments.

Amplification

The ligation products of the above step are then amplified using biotinylated forward and reverse primers: 5'-Biotin-GGA TTT GCT GGT CGA GTA CA (SEQ ID NO: 94) and 5'-Biotin-CGT TCG AGC TCA CGT AGA TGT C (SEQ ID NO: 95), respectively, where the reverse primer will not contribute to the amplification process until its complement is formed when one round of copying of fragments with the forward primer is completed.

Digestion and Purification and Sequencing of the $F_iD$-GSTs

The amplification products are digested with NlaIII and the tags are separated from the duplex linker and the duplex amplification adapter digestion products by capturing the biotinylated ends on streptavidin beads. The tags, free in solution are processed for sequencing, using the methods outlined for the general GST procedures, i.e., either by concatemer formation, cloning and sequencing or by limiting dilution, individual amplification and sequencing by pyrosequencing or capillary electrophoresis.

Correlation of FD-GSTs with DNA Binding Protein-Regulated Genes

The sequences of the identified tags are located in the genome of the studied organism to correlate the binding protein of interest and the gene(s) regulated by it and relate that to the physiological conditions of the starting cellular material.

TABLE 1

Predicted GSTs for *Y. pestis* EV766

| | NotI fragmentation [64 fragments] | | BamHI fragmentation [699 fragments] | |
|---|---|---|---|---|
| | start[a] | after MmeI digestion | start[a] | after MmeI digestion |
| Tags of Length ≤21 | | | | |
| Predicted Tags | 115 (7) | 115 (7) | 1236 (96) | 1214 (93) |
| Unique Tags | 115 (7) | 115 (7) | 1203 (94) | 1181 (91) |
| Single Tags | 115 (7) | 115 (7) | 1189 (92) | 1167 (89) |
| Multiple Tags | 0 | 0 | 14 (2) | 14 (2) |
| Tags of Length ≤20 | | | | |
| Predicted Tags | 7 (0) | 7 (0) | 89 (12) | 89 (12) |
| Unique Tags | 7 (0) | 7 (0) | 86 (12) | 86 (12) |
| Single Tags | 7 (0) | 7 (0) | 84 (12) | 84 (12) |
| Multiple Tags | 0 | 0 | 2 (0) | 0 |
| Zero Length Tags[b] | 4 | 4 | 1 | 1 |
| SU | 126 (7) | 126 (7) | 1326 (108) | 1303 (105) |

[a]Values in parentheses are the numbers of tags with ambiguous directions, i.e., they begin with sequence CATGAA.
[b]Zero length tags occur when the fragmenting site is immediately adjacent to an NlaIII site.

TABLE 2

Correspondence Between Predicted and Actual GST Frequencies

| | | FREQUENCY | |
|---|---|---|---|
| SEQ ID NO | GST[a] | predicted | actual |
| 14 | ATCTGGAGGTTCGGTTC | 8 | 65 |
| 15 | CGTCATCTCGCTGAACG | 7 | 45 |
| 16 | GATGTATTTACGGCGTC | 5 | 34 |
| 17 | CCCTGCGGTACGGGAGC | 3 | 34 |
| 18 | GCTGCATTGGCACCGTT | 2 | 23 |

TABLE 2-continued

Correspondence Between Predicted and Actual GST Frequencies

| | | FREQUENCY | |
|---|---|---|---|
| SEQ ID NO | GST[a] | predicted | actual |
| 19 | CCAGCATCAGCCAGCGC | 2 | 22 |
| 20 | TAGGCTCGAGCCGCGCC | 3 | 20 |
| 21 | TCGTTCAAATCAAAGGA | 4 | 13 |
| 22 | CTGATAAACCGGGATCG | 2 | 13 |
| 23 | AATCCTCACCTAACCGA | 2 | 12 |
| 24 | CTTTCGTTGGTTAGCGA | 3 | 11 |
| 25 | CCCCAGCCCTGGCCCGC | 2 | 11 |
| 26 | AACCGCGTATCAATCAG | 2 | 11 |
| 27 | TGCGTTTTCAGGACGGT | 2 | 9 |
| 28 | TTGGATCCGAAGGGGTT | 3 | unseen-contains BamHI site |
| 29 | GGGATCCGAAGGGGTTC | 2 | unseen-contains BamHI site |

[a]CATG omitted

TABLE 3

Potential Deletions in the *Y. pestis* EV766 genome

| Start-End | Position by | IS Element | # of Tags Affected |
|---|---|---|---|
| F314-F327 | 2,172,627 - 2,254,447 | yes, IS100 | 25 |
| R194-R197 | 1,307,243 - 1,316,087 | yes, IS1541 | 7 |
| F227-F228 | 1,554,643 - 1,556,368 | no | 3 |
| F237-F238 | 1,618,033 - 1,652,133 | yes, IS100 | 3 |
| F381-F382 | 2,662,263 - 2,685,036 | no | 3 |
| F453-F454 | 3,069,009 - 3,122,266 | no | 3 |
| | | Total | 44 |

TABLE 4

Shared GSTs Between Two Different Bacteria[a]

| SEQ ID NO | GST sequence[b] | organisms | total | organism (count) | organism (count) |
|---|---|---|---|---|---|
| 30 | GCCGCTTAACCGCCGCA | 2 | 4 | *Escherichia coli* (3) | *Yersinia pestis* (1) |
| 31 | GATCGCCGATCGTCCCG | 2 | 3 | *Mycobacterium leprae* (1) | *Mycobacterium tuberculosis* (2) |
| 32 | GCAACGATATTGGTGAC | 2 | 3 | *Mycobacterium leprae* (1) | *Mycobacterium tuberculosis* (2) |
| 33 | CCGCCCCGGAAATCACC | 2 | 3 | *Mycobacterium leprae* (1) | *Mycobacterium tuberculosis* (2) |
| 34 | GACCTGTCCACCGGCAA | 2 | 3 | *Mycobacterium leprae* (1) | *Mycobacterium tuberculosis* (2) |
| 35 | GGCTGTGGGTGGCGTTC | 2 | 3 | *Mycobacterium leprae* (1) | *Mycobacterium tuberculosis* (2) |
| 36 | CTTGGCCGCTACACCAC | 2 | 3 | *Pyrococcus abyssi* (1) | *Pyrococcus horikoshii* (2) |
| 37 | CTCCGCCGCTTGTGCGG | 2 | 3 | *Mycobacterium leprae* (1) | *Mycobacterium tuberculosis* (2) |
| 38 | GTGGATGCCTTGGCATC | 2 | 3 | *Mycobacterium leprae* (1) | *Mycobacterium tuberculosis* (2) |
| 39 | GCGACCCAGGAACAGCA | 2 | 3 | *Mycobacterium leprae* (1) | *Mycobacterium tuberculosis* (2) |
| 40 | GGAGTCGATGTTATCGG | 2 | 3 | *Mycobacterium leprae* (1) | *Mycobacterium tuberculosis* (2) |
| 41 | AAGCCGGTCGCCATCAT | 2 | 2 | *Mesorhizobium loti* (1) | *Sinorhizobium meliloti* (1) |
| 42 | GTGACTTCTGCGGATGT | 2 | 2 | *Chlamydia muridarum* (1) | *Chlamydia trachomatis* (1) |
| 43 | TGCACCGGAATGCGGAT | 2 | 2 | *Mesorhizobium loti* (1) | *Sinorhizobium meliloti* (1) |
| 44 | CACCACCTCTCCTTCTA | 2 | 2 | *Thermoplasma acidophilum* (1) | *Thermoplasma volcanium* (1) |

TABLE 4-continued

Shared GSTs Between Two Different Bacteria[a]

| SEQ ID NO | GST sequence[b] | organisms | total | organism (count) | organism (count) |
|---|---|---|---|---|---|
| 45 | TCGGACAGAACCTTGCG | 2 | 2 | *Agrobacterium tumefaciens* (1) | *Sinorhizobium meliloti* (1) |
| 46 | ACGCCGAAGGTGATGGC | 2 | 2 | *Mesorhizobiumloti* (1) | *Sinorhizobium meliloti* (1) |
| 47 | AACGAAGATCAATTTCC | 2 | 2 | *Chlamydia muridarum* (1) | *Chlamydia trachomatis* (1) |
| 48 | AATTAGAAAATTATGAC | 2 | 2 | *Haemophilus influenzae* (1) | *Pasteurella multocida* (1) |
| 49 | CGGACTTCGGTCGGCTT | 2 | 2 | *Mesorhizobium loti* (1) | *Sinorhizobium meliloti* (1) |
| 50 | CTCTCAACGTAGGGAAC | 2 | 2 | *Pyrococcus abyssi* (1) | *Pyrococcus horikoshii* (1) |
| 51 | CCCATCACTATCAAGCC | 2 | 2 | *Chlamydia muridarum* (1) | *Chlamydia trachomatis* (1) |
| 52 | AGCAGGTTGAAGGTTGA | 2 | 2 | *Mycoplasma genitalium* (1) | *Mycoplasma pneumoniae* (1) |
| 53 | ATGCGCAAGTGCCATCT | 2 | 2 | *Agrobacterium tumefaciens* (1) | *Sinorhizobium meliloti* (1) |
| 54 | CAGGTCGGCATTTAACC | 2 | 2 | *Pyrococcus abyssi* (1) | *Pyrococcus horikoshii* (1) |
| 55 | AAGGTTCAACGTGGGTC | 2 | 2 | *Thermoplasma acidophilum* (1) | *Thermoplasma volcanium* (1) |
| 56 | CGGGGAAACGTAGTAGC | 2 | 2 | *Chlamydia muridarum* (1) | *Chlamydia trachomatis* (1) |
| 57 | CACAAGATCCAGGACCG | 2 | 2 | *Mesorhizobium loti* (1) | *Sinorhizobium meliloti* (1) |
| 58 | AGCTAACCCCATTTTGT | 2 | 2 | *Chlamydia muridarum* (1) | *Chlamydia trachomatis* (1) |
| 59 | CAGCACTCCATATTTTA | 2 | 2 | *Clostridium acetobutylicum* (1) | *Pyrococcus horikoshii* (1) |

[a]GSTs within 25 by of the BamHI fragmentation site were omitted;
[b]CATG omitted

What is claimed is:

1. A method for identifying methyl CpG island-associated genome signature tags comprising:
   a) providing a sample containing genomic DNA;
   b) isolating the genomic DNA from the sample;
   c) contacting the isolated DNA from step b) with a fragmenting type II restriction enzyme, said fragmenting restriction enzyme having a low probability of cleaving G-C rich DNA sequences, under conditions appropriate for substantially complete digestion of the DNA, thereby generating a plurality of DNA fragment species, each having complementary cohesive termini;
   d) separating methylated CpG island (Me-CpGI) fragments from fragments in which CpG sequences are not methylated by contacting the DNA fragment species of step c) with an affinity resin that specifically recognizes and binds Me-CpG sequences thereby capturing the Me-CpGI fragments on the resin;

e) incubating the captured Me-CpGI fragments with a molar excess of duplex linker having a type IIS restriction enzyme recognition sequence and one cohesive terminus compatible with termini generated by the fragmenting restriction enzyme, under conditions appropriate for ligating one duplex linker to each terminus of the captured fragments of step d);

f) contacting the ligation products of step e) with the type IIS restriction enzyme, under conditions appropriate for complete digestion of the captured Me-CpGI fragments, thereby releasing the duplex linkers and appended Me-CpGI-associated signature tags;

g) recovering the released linkers and appended tags;

h) incubating the recovered linkers and tags of step g) with a molar excess of an amplification adapter having one terminus compatible with the termini of the appended signature tags under conditions appropriate for ligation of one amplification adapter to each appended signature tag;

i) recovering the ligation products of step h);

j) determining the nucleotide sequence of a statistically significant number of appended signature tags to generate a listing of methyl CpG Island-associated signature tags, thereby identifying methyl CpG Island-associated genome signature tags.

2. The method of claim 1 in which the fragmenting type II restriction enzyme is selected from the group consisting of Tsp509I, MseI, AseI, SalI, ApaLI and EcoRI.

3. The method according to claim 2 wherein the type IIS restriction enzyme is MmeI; and, the nucleotide sequence is determined by either capillary gel electrophoresis or pyrosequencing.

4. The method according to claim 1 wherein the amplification adapter is part of a collection comprising amplification adapters with degenerate overhang sequences.

5. The method according to claim 4 wherein the amplification adapter is part of a collection comprising amplification adapters with a subset of degenerate overhang sequences.

* * * * *

```
                               SEQUENCE LISTING

<160> NUMBER OF SEQ ID NOS: 95

<210> SEQ ID NO 1
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 1 cgaaccccett cg                                                          12

<210> SEQ ID NO 2
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 2
gatccgaagg ggttcgt                                                      17

<210> SEQ ID NO 3
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 3
tttggatttg ctggtcgagt acaactaggc ttaatccgac atg                         43

<210> SEQ ID NO 4
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 4
tcggattaag cctagttgta ctcgaccagc aaatcc                                 36
```

<210> SEQ ID NO 5
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 5
ttcatggcgg agacgtccgc cactagtgtc gcaactgact a                41

<210> SEQ ID NO 6
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(43)
<223> OTHER INFORMATION: n is a, c, g, or t

<400> SEQUENCE: 6
tagtcagttg cgacactagt ggcggacgtc tccgccatga ann              43

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ggatttgctg gtcgagtaca                                         20

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
tagtcagttg cgacactagt ggc                                     23

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
catgcagggt gcacgacccg a                                       21

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
catgtggccg ccgcgcttaa                                         20

<210> SEQ ID NO 11
<211> LENGTH: 21
<212> TYPE: DNA
<213> ORGANISM: Artificial Sequence -continued
<220> FEATURE:
<223> OTHER INFORMATION: Primer

<400> SEQUENCE: 11
catgactctg ccatagcttc g 21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
catgcaggac cgcggacaat g 21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
catgcagtgc catcctcacg g 21

<210> SEQ ID NO 14
<211> LENGTH: 17
<212> TYPE: DNA
<213> ORGANISM: Yersinia pestis

<400> SEQUENCE: 14
atctggaggt tcggttc 17

<210> SEQ ID NO 15
<211> LENGTH: 17
<212> TYPE: DNA
<213> ORGANISM: Yersinia pestis

<400> SEQUENCE: 15
cgtcatctcg ctgaacg 17

<210> SEQ ID NO 16
<211> LENGTH: 17
<212> TYPE: DNA
<213> ORGANISM: Yersinia pestis

<400> SEQUENCE: 16
gatgtattta cggcgtc 17

<210> SEQ ID NO 17
<211> LENGTH: 17
<212> TYPE: DNA
<213> ORGANISM: Yersinia pestis

<400> SEQUENCE: 17
ccctgcggta cgggagc 17

<210> SEQ ID NO 18
<211> LENGTH: 17
<212> TYPE: DNA
<213> ORGANISM: Yersinia pestis

<400> SEQUENCE: 18
gctgcattgg caccgtt 17

```
<210> SEQ ID NO 19
<211> LENGTH: 17
<212> TYPE: DNA
<213> ORGANISM: Yersinia pestis

<400> SEQUENCE: 19
ccagcatcag ccagcgc                                                   17

<210> SEQ ID NO 20
<211> LENGTH: 17
<212> TYPE: DNA
<213> ORGANISM: Yersinia pestis

<400> SEQUENCE: 20
taggctcgag ccgcgcc                                                   17

<210> SEQ ID NO 21
<211> LENGTH: 17
<212> TYPE: DNA
<213> ORGANISM: Yersinia pestis

<400> SEQUENCE: 21
tcgttcaaat caaagga                                                   17

<210> SEQ ID NO 22
<211> LENGTH: 17
<212> TYPE: DNA
<213> ORGANISM: Yersinia pestis

<400> SEQUENCE: 22
ctgataaacc gggatcg                                                   17

<210> SEQ ID NO 23
<211> LENGTH: 17
<212> TYPE: DNA
<213> ORGANISM: Yersinia pestis

<400> SEQUENCE: 23
aatcctcacc taaccga                                                   17

<210> SEQ ID NO 24
<211> LENGTH: 17
<212> TYPE: DNA
<213> ORGANISM: Yersinia pestis

<400> SEQUENCE: 24
ctttcgttgg ttagcga                                                   17

<210> SEQ ID NO 25
<211> LENGTH: 17
<212> TYPE: DNA
<213> ORGANISM: Yersinia pestis

<400> SEQUENCE: 25
ccccagccct ggcccgc                                                   17

<210> SEQ ID NO 26
<211> LENGTH: 17
<212> TYPE: DNA
<213> ORGANISM: Yersinia pestis

<400> SEQUENCE: 26
aaccgcgtat caatcag                                                   17
```

-continued

```
<210> SEQ ID NO 27
<211> LENGTH: 17
<212> TYPE: DNA
<213> ORGANISM: Yersinia pestis

<400> SEQUENCE: 27
tgcgttttca ggacggt                                                  17

<210> SEQ ID NO 28
<211> LENGTH: 17
<212> TYPE: DNA
<213> ORGANISM: Yersinia pestis

<400> SEQUENCE: 28
ttggatccga aggggtt                                                  17

<210> SEQ ID NO 29
<211> LENGTH: 17
<212> TYPE: DNA
<213> ORGANISM: Yersinia pestis

<400> SEQUENCE: 29
gggatccgaa ggggttc                                                  17

<210> SEQ ID NO 30
<211> LENGTH: 17
<212> TYPE: DNA
<213> ORGANISM: Artificial Sequence
<220> FEATURE:
<223> OTHER INFORMATION: found in Yersinia pestis and Escherichia coli

<400> SEQUENCE: 30
gccgcttaac cgccgca                                                  17

<210> SEQ ID NO 31
<211> LENGTH: 17
<212> TYPE: DNA
<213> ORGANISM: Artificial Sequence
<220> FEATURE:
<223> OTHER INFORMATION: found in Mycobacterium leprae and Mycobacterium
      tuberculosis

<400> SEQUENCE: 31
gatcgccgat cgtcccg                                                  17

<210> SEQ ID NO 32
<211> LENGTH: 17
<212> TYPE: DNA
<213> ORGANISM: Artificial Sequence
<220> FEATURE:
<223> OTHER INFORMATION: found in Mycobacterium leprae and Mycobacterium
      tuberculosis

<400> SEQUENCE: 32
gcaacgatat tggtgac                                                  17

<210> SEQ ID NO 33
<211> LENGTH: 17
<212> TYPE: DNA
<213> ORGANISM: Artificial Sequence
<220> FEATURE:
<223> OTHER INFORMATION: found in Mycobacterium leprae and Mycobacterium
      tuberculosis

<400> SEQUENCE: 33
ccgccccgga aatcacc                                                  17
```

```
<210> SEQ ID NO 34
<211> LENGTH: 17
<212> TYPE: DNA
<213> ORGANISM: Artificial Sequence
<220> FEATURE:
<223> OTHER INFORMATION: found in Mycobacterium leprae and Mycobacterium
      tuberculosis

<400> SEQUENCE: 34
gacctgtcca ccggcaa                                                  17

<210> SEQ ID NO 35
<211> LENGTH: 17
<212> TYPE: DNA
<213> ORGANISM: Artificial Sequence
<220> FEATURE:
<223> OTHER INFORMATION: found in Mycobacterium leprae and Mycobacterium
      tuberculosis

<400> SEQUENCE: 35
ggctgtgggt ggcgttc                                                  17

<210> SEQ ID NO 36
<211> LENGTH: 17
<212> TYPE: DNA
<213> ORGANISM: Artificial Sequence
<220> FEATURE:
<223> OTHER INFORMATION: found in Pyrococcus abyssi and Pyrococcus
      horikoshii

<400> SEQUENCE: 36
cttggccgct acaccac                                                  17

<210> SEQ ID NO 37
<211> LENGTH: 17
<212> TYPE: DNA
<213> ORGANISM: Artificial Sequence
<220> FEATURE:
<223> OTHER INFORMATION: found in Mycobacterium leprae and Mycobacterium
      tuberculosis

<400> SEQUENCE: 37
ctccgccgct tgtgcgg                                                  17

<210> SEQ ID NO 38
<211> LENGTH: 17
<212> TYPE: DNA
<213> ORGANISM: Artificial Sequence
<220> FEATURE:
<223> OTHER INFORMATION: found in Mycobacterium leprae and Mycobacterium
      tuberculosis

<400> SEQUENCE: 38
gtggatgcct tggcatc                                                  17

<210> SEQ ID NO 39
<211> LENGTH: 17
<212> TYPE: DNA
<213> ORGANISM: Artificial Sequence
<220> FEATURE:
<223> OTHER INFORMATION: found in Mycobacterium leprae and Mycobacterium
      tuberculosis

<400> SEQUENCE: 39
gcgacccagg aacagca                                                  17
```

```
<210> SEQ ID NO 40
<211> LENGTH: 17
<212> TYPE: DNA
<213> ORGANISM: Artificial Sequence
<220> FEATURE:
<223> OTHER INFORMATION: found in Mycobacterium leprae and Mycobacterium
      tuberculosis

<400> SEQUENCE: 40
ggagtcgatg ttatcgg                                                      17

<210> SEQ ID NO 41
<211> LENGTH: 17
<212> TYPE: DNA
<213> ORGANISM: Artificial Sequence
<220> FEATURE:
<223> OTHER INFORMATION: found in Mesorhizobium loti and Sinorhizobium
      meliloti

<400> SEQUENCE: 41
aagccggtcg ccatcat                                                      17

<210> SEQ ID NO 42
<211> LENGTH: 17
<212> TYPE: DNA
<213> ORGANISM: Artificial Sequence
<220> FEATURE:
<223> OTHER INFORMATION: found in Chlamydia muridarum and Clamydia
      trachomatis

<400> SEQUENCE: 42
gtgacttctg cggatgt                                                      17

<210> SEQ ID NO 43
<211> LENGTH: 17
<212> TYPE: DNA
<213> ORGANISM: Artificial Sequence
<220> FEATURE:
<223> OTHER INFORMATION: found in Mesorhizobium loti and Sinorhizobium
      meliloti

<400> SEQUENCE: 43
tgcaccggaa tgcggat                                                      17

<210> SEQ ID NO 44
<211> LENGTH: 17
<212> TYPE: DNA
<213> ORGANISM: Artificial Sequence
<220> FEATURE:
<223> OTHER INFORMATION: found in Thermoplasma acidophilum and
      Thermoplasma volcanium

<400> SEQUENCE: 44
caccacctct ccttcta                                                      17

<210> SEQ ID NO 45
<211> LENGTH: 17
<212> TYPE: DNA
<213> ORGANISM: Artificial Sequence
<220> FEATURE:
<223> OTHER INFORMATION: found in Agrobacterium tumefaciens and
      Sinorhizobium meliloti

<400> SEQUENCE: 45
tcggacagaa ccttgcg                                                      17
```

-continued

```
<210> SEQ ID NO 46
<211> LENGTH: 17
<212> TYPE: DNA
<213> ORGANISM: Artificial Sequence
<220> FEATURE:
<223> OTHER INFORMATION: found in Mesorhizobium loti and Sinorhizobium
      meliloti

<400> SEQUENCE: 46
acgccgaagg tgatggc                                                  17

<210> SEQ ID NO 47
<211> LENGTH: 17
<212> TYPE: DNA
<213> ORGANISM: Artificial Sequence
<220> FEATURE:
<223> OTHER INFORMATION: found in Chlamydia muridarum and Chlamydia
      trachomatis

<400> SEQUENCE: 47
aacgaagatc aatttcc                                                  17

<210> SEQ ID NO 48
<211> LENGTH: 17
<212> TYPE: DNA
<213> ORGANISM: Artificial Sequence
<220> FEATURE:
<223> OTHER INFORMATION: found in Haemophilus influenzae and Pasteurella
      multocida

<400> SEQUENCE: 48
aattagaaaa ttatgac                                                  17

<210> SEQ ID NO 49
<211> LENGTH: 17
<212> TYPE: DNA
<213> ORGANISM: Artificial Sequence
<220> FEATURE:
<223> OTHER INFORMATION: found in Mesorhizobium loti and Sinorhizobium
      meliloti

<400> SEQUENCE: 49
cggacttcgg tcggctt                                                  17

<210> SEQ ID NO 50
<211> LENGTH: 17
<212> TYPE: DNA
<213> ORGANISM: Artificial Sequence
<220> FEATURE:
<223> OTHER INFORMATION: found in Pyrococcus abyssi and Pyrococcus
      horikoshii

<400> SEQUENCE: 50
ctctcaacgt agggaac                                                  17

<210> SEQ ID NO 51
<211> LENGTH: 17
<212> TYPE: DNA
<213> ORGANISM: Artificial Sequence
<220> FEATURE:
<223> OTHER INFORMATION: found in Chlamydia muridarum and Chlamydia
      trachomatis

<400> SEQUENCE: 51
cccatcacta tcaagcc                                                  17
```

```
<210> SEQ ID NO 52
<211> LENGTH: 17
<212> TYPE: DNA
<213> ORGANISM: Artificial Sequence
<220> FEATURE:
<223> OTHER INFORMATION: found in Mycoplasma genitalium and Mycoplasma
      pneumoniae

<400> SEQUENCE: 52
agcaggttga aggttga                                                    17

<210> SEQ ID NO 53
<211> LENGTH: 17
<212> TYPE: DNA
<213> ORGANISM: Artificial Sequence
<220> FEATURE:
<223> OTHER INFORMATION: found in Agrobacterium tumefaciens and
      Sinorhizobium meliloti

<400> SEQUENCE: 53
atgcgcaagt gccatct                                                    17

<210> SEQ ID NO 54
<211> LENGTH: 17
<212> TYPE: DNA
<213> ORGANISM: Artificial Sequence
<220> FEATURE:
<223> OTHER INFORMATION: found in Pyrococcus abyssi and Pyrococcus
      horikoshii

<400> SEQUENCE: 54
caggtcggca tttaacc                                                    17

<210> SEQ ID NO 55
<211> LENGTH: 17
<212> TYPE: DNA
<213> ORGANISM: Artificial Sequence
<220> FEATURE:
<223> OTHER INFORMATION: found in Thermoplasma acidophilum and
      Thermoplasma volcanium

<400> SEQUENCE: 55
aaggttcaac gtgggtc                                                    17

<210> SEQ ID NO 56
<211> LENGTH: 17
<212> TYPE: DNA
<213> ORGANISM: Artificial Sequence
<220> FEATURE:
<223> OTHER INFORMATION: found in Chlamydia muridarum and Chlamydia
      trachomatis

<400> SEQUENCE: 56
cggggaaacg tagtagc                                                    17

<210> SEQ ID NO 57
<211> LENGTH: 17
<212> TYPE: DNA
<213> ORGANISM: Artificial Sequence
<220> FEATURE:
<223> OTHER INFORMATION: found in Mesorhizobium loti and Sinorhizobium
      meliloti

<400> SEQUENCE: 57
cacaagatcc aggaccg                                                    17
```

```
<210> SEQ ID NO 58
<211> LENGTH: 17
<212> TYPE: DNA
<213> ORGANISM: Artificial Sequence
<220> FEATURE:
<223> OTHER INFORMATION: found in Chlamydia muridarum and Chlamydia
      trachomatis

<400> SEQUENCE: 58
agctaacccc attttgt                                                  17

<210> SEQ ID NO 59
<211> LENGTH: 17
<212> TYPE: DNA
<213> ORGANISM: Artificial Sequence
<220> FEATURE:
<223> OTHER INFORMATION: found in Clostridium acetobutylicum and
      Pyrococcus horikoshii

<400> SEQUENCE: 59
cagcactcca tatttta                                                  17

<210> SEQ ID NO 60
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 60
cgtaatacga ctcactatag gga                                           23

<210> SEQ ID NO 61
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 61
gatctcccta tagtgagtcg tattacg                                       27

<210> SEQ ID NO 62
<211> LENGTH: 20
<212> TYPE: DNA
<213> ORGANISM: Deinococcus radiodurans

<400> SEQUENCE: 62
gtacggcgcg gacgctctgc                                               20

<210> SEQ ID NO 63
<211> LENGTH: 20
<212> TYPE: DNA
<213> ORGANISM: Deinococcus radiodurans

<400> SEQUENCE: 63
gtactatttc tgagcctcga                                               20

<210> SEQ ID NO 64
<211> LENGTH: 20
<212> TYPE: DNA
<213> ORGANISM: Homo sapiens

<400> SEQUENCE: 64
ttaattccga taacgaacga                                               20
```

```
<210> SEQ ID NO 65
<211> LENGTH: 20
<212> TYPE: DNA
<213> ORGANISM: Homo sapiens

<400> SEQUENCE: 65
ttaaacagtt gggctgcgct                                                     20

<210> SEQ ID NO 66
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 66
tttggatttg ctggtcgaat tcaactaggc ttaatccgac g                             41

<210> SEQ ID NO 67
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 67
tacgtcggat taagcctagt tgaatt                                              26

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
ctgagccagg atcaaactct                                                     20

<210> SEQ ID NO 69
<211> LENGTH: 22
<212> TYPE: DNA
<213> ORGANISM: Artificial Sequence
<220> FEATURE:
<223> OTHER INFORMATION: Primer

<400> SEQUENCE: 69
ggatttgctg gtcgaattca ac                                                  22

<210> SEQ ID NO 70
<211> LENGTH: 58
<212> TYPE: DNA
<213> ORGANISM: Artificial Sequence
<220> FEATURE:
<223> OTHER INFORMATION: Linker oligonucleotide
<220> FEATURE:
<221> NAME/KEY: misc_feature
<222> LOCATION: (42)..(58)
<223> OTHER INFORMATION: n = a, t, c, or g

<400> SEQUENCE: 70
ggatttgctg gtcgaattca actaggctta atccgacgta cnnnnnnnnn nnnnnnnn          58

<210> SEQ ID NO 71
<211> LENGTH: 56
<212> TYPE: DNA
<213> ORGANISM: Artificial Sequence
<220> FEATURE:
<223> OTHER INFORMATION: Linker oligonucleotide
```

```
<220> FEATURE:
<221> NAME/KEY: misc_feature
<222> LOCATION: (1)..(15)
<223> OTHER INFORMATION: n is a, t, c, or g

<400> SEQUENCE: 71
nnnnnnnnnn nnnnngtacg tcggattaag cctagttgaa ttcgaccagc aaatcc        56

<210> SEQ ID NO 72
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 72
tttgtacggc ggagacgtcc gccactagtg tcgcaactga cta                      43

<210> SEQ ID NO 73
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(45)
<223> OTHER INFORMATION: n = a, t, c, or g

<400> SEQUENCE: 73
tagtcagttg cgacactagt ggcggacgtc tccgccgtac aaann                    45

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
ggatttgctg gtcgaattca                                                20

<210> SEQ ID NO 75
<211> LENGTH: 23
<212> TYPE: DNA
<213> ORGANISM: Artificial Sequence
<220> FEATURE:
<223> OTHER INFORMATION: Primer

<400> SEQUENCE: 75
tagtcagttg cgacactagt ggc                                            23

<210> SEQ ID NO 76
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 76
tttggatttg ctggtcgagt acaactaggc taatccgact                          40

<210> SEQ ID NO 77
<211> LENGTH: 39
<212> TYPE: DNA
<213> ORGANISM: Artificial Sequence
<220> FEATURE:
<223> OTHER INFORMATION: Synthetic oligonucleotide
```

```
<400> SEQUENCE: 77
taagtcggat tagcctagtt gtactcgacc agcaaatcc                                  39

<210> SEQ ID NO 78
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 78
cccttaagcg gagacgtccg ccactagtgt cgcaactgac ta                              42

<210> SEQ ID NO 79
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(44)
<223> OTHER INFORMATION: n = a, t, c, or g

<400> SEQUENCE: 79
tagtcagttg cgacactagt ggcggacgtc tccgcttaag ggnn                            44

<210> SEQ ID NO 80
<211> LENGTH: 41
<212> TYPE: DNA
<213> ORGANISM: Artificial Sequence
<220> FEATURE:
<223> OTHER INFORMATION: Linker oliognucleotide

<400> SEQUENCE: 80
tccggtctac tgaattccga accgaggagg gcccatccga c                               41

<210> SEQ ID NO 81
<211> LENGTH: 12
<212> TYPE: DNA
<213> ORGANISM: Artificial Sequence
<220> FEATURE:
<223> OTHER INFORMATION: Linker oligonucleotide

<400> SEQUENCE: 81
gtcggatggg cc                                                               12

<210> SEQ ID NO 82
<211> LENGTH: 22
<212> TYPE: DNA
<213> ORGANISM: Artificial Sequence
<220> FEATURE:
<223> OTHER INFORMATION: Primer

<400> SEQUENCE: 82
tccggtctac tgaattccga ac                                                    22

<210> SEQ ID NO 83
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 83
catgacgcta cgtccgtgtt gtcggtcctg                                            30
```

<210> SEQ ID NO 84
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (31)..(32)
<223> OTHER INFORMATION: n = a, t, c, or g

<400> SEQUENCE: 84
actacgcacc ggacgagacg tagcgtcatg nn                                  32

<210> SEQ ID NO 85
<211> LENGTH: 22
<212> TYPE: DNA
<213> ORGANISM: Artificial Sequence
<220> FEATURE:
<223> OTHER INFORMATION: Primer

<400> SEQUENCE: 85
tccggtctac tgaattccga ac                                             22

<210> SEQ ID NO 86
<211> LENGTH: 21
<212> TYPE: DNA
<213> ORGANISM: Artificial Sequence
<220> FEATURE:
<223> OTHER INFORMATION: Primer

<400> SEQUENCE: 86
actacgcacc ggacgagacg t                                              21

<210> SEQ ID NO 87
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 87
tccggtctac tgaattccga accccttgcg gccgc                               35

<210> SEQ ID NO 88
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 88
gcggccgcaa gggg                                                      14

<210> SEQ ID NO 89
<211> LENGTH: 22
<212> TYPE: DNA
<213> ORGANISM: Artificial Sequence
<220> FEATURE:
<223> OTHER INFORMATION: Primer

<400> SEQUENCE: 89
tccggtctac tgaattccga ac                                             22

<210> SEQ ID NO 90
<211> LENGTH: 43
<212> TYPE: DNA
<213> ORGANISM: Artificial Sequence

```
<220> FEATURE:
<223> OTHER INFORMATION: Synthetic oligonucleotide

<400> SEQUENCE: 90
tttggatttg ctggtcgagt acaactaggc ttaatccgac atg              43

<210> SEQ ID NO 91
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 91
tcggattaag cctagttgta ctcgaccagc aaatcc                      36

<210> SEQ ID NO 92
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 92
tttcatggcg gagacgtccg ccactagtgt cgcaactgac ta               42

<210> SEQ ID NO 93
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n = a, t, c, or g

<400> SEQUENCE: 93
nnaaagtacc gcctctgcag gctgtagatg cactcgagct tgc              43

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
ggatttgctg gtcgagtaca                                        20

<210> SEQ ID NO 95
<211> LENGTH: 22
<212> TYPE: DNA
<213> ORGANISM: Artificial Sequence
<220> FEATURE:
<223> OTHER INFORMATION: Primer

<400> SEQUENCE: 95
cgttcgagct cacgtagatg tc                                     22
```